US011141452B2

(12) United States Patent
Hruby et al.

(10) Patent No.: US 11,141,452 B2
(45) Date of Patent: Oct. 12, 2021

(54) BIFUNCTIONAL COMPOUNDS FOR RELIEF OF PAIN COMPRISING AN OPIOID RECEPTOR AGONIST MOIETY AND A NK1 RECEPTOR ANTAGONIST MOIETY AND METHODS FOR TREATING PAIN

(71) Applicant: THE ARIZONA BOARD OF REGENTS ON BEHALF OF THE UNIVERSITY OF ARIZONA, Tucson, AZ (US)

(72) Inventors: Victor J. Hruby, Tucson, AZ (US); Aswini K. Giri, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/121,270

(22) PCT Filed: Feb. 24, 2015

(86) PCT No.: PCT/US2015/017324
§ 371 (c)(1),
(2) Date: Aug. 24, 2016

(87) PCT Pub. No.: WO2015/127451
PCT Pub. Date: Aug. 27, 2015

(65) Prior Publication Data
US 2016/0361378 A1 Dec. 15, 2016

Related U.S. Application Data

(60) Provisional application No. 61/943,820, filed on Feb. 24, 2014.

(51) Int. Cl.
| | |
|---|---|
| *C07K 7/06* | (2006.01) |
| *C07K 7/00* | (2006.01) |
| *C07K 7/22* | (2006.01) |
| *C07K 14/00* | (2006.01) |
| *A61K 38/00* | (2006.01) |
| *A61K 38/08* | (2019.01) |
| *A61K 38/46* | (2006.01) |
| *A61K 38/17* | (2006.01) |
| *A61K 38/04* | (2006.01) |
| *A61K 47/65* | (2017.01) |
| *A61K 47/64* | (2017.01) |
| *A61P 23/00* | (2006.01) |
| *A61P 25/04* | (2006.01) |
| *A61P 25/00* | (2006.01) |
| *A61P 23/02* | (2006.01) |
| *A61P 25/02* | (2006.01) |
| *A61K 38/07* | (2006.01) |

(52) U.S. Cl.
CPC ............ *A61K 38/046* (2013.01); *A61K 38/07* (2013.01); *A61K 38/1787* (2013.01); *A61K 47/64* (2017.08); *A61K 47/65* (2017.08); *A61P 23/00* (2018.01); *A61P 23/02* (2018.01); *A61P 25/00* (2018.01); *A61P 25/02* (2018.01); *A61P 25/04* (2018.01); *C07K 7/06* (2013.01)

(58) Field of Classification Search
CPC .... A61K 2300/00; A61K 38/00; A61K 47/55; A61K 47/64; A61K 38/046; A61K 47/65; A61K 38/08; C07K 7/08; C07K 14/00; C07K 14/4705; C07K 14/705; C07K 2319/00; C07K 14/47; C07K 19/00; C07K 2319/32; C07K 7/06; A61P 23/00; A61P 25/04; A61P 29/00; A61P 25/02; A61P 25/28
See application file for complete search history.

(56) References Cited

U.S. PATENT DOCUMENTS

| | | | |
|---|---|---|---|
| 4,649,200 A | 3/1987 | Portoghese et al. | |
| 5,245,046 A | 9/1993 | Youngdale et al. | |
| 5,891,842 A | 4/1999 | Kream | |
| 6,638,981 B2 * | 10/2003 | Williams | ............. A61K 9/0014 424/448 |
| 6,759,520 B1 | 7/2004 | Carr et al. | |
| 6,855,807 B1 | 2/2005 | Devi et al. | |
| 6,875,759 B1 | 4/2005 | Lipkowski et al. | |
| 6,881,829 B2 | 4/2005 | Kream | |
| 6,913,760 B2 | 7/2005 | Carr et al. | |
| 8,026,218 B2 * | 9/2011 | Hruby | ...................... C07K 7/06 514/18.3 |
| 8,729,070 B2 * | 5/2014 | Glozman | ............. A61K 31/138 514/220 |

(Continued)

FOREIGN PATENT DOCUMENTS

| | | |
|---|---|---|
| WO | WO2001007029 A2 | 2/2001 |
| WO | WO2001030371 A2 | 5/2001 |

(Continued)

OTHER PUBLICATIONS

Bowie et al. Science, 1990, 247:1306-1310.*

(Continued)

*Primary Examiner* — Chang-Yu Wang
(74) *Attorney, Agent, or Firm* — Don D. Cha; HDC Intellectual Property Law, LLP

(57) ABSTRACT

A compound for treatment of pain comprising a single multivalent/multifunctional ligand with agonist activity at opioid receptors and with antagonist activity at NK-1 receptors, joined by a linker. Also disclosed is a pharmaceutical compound comprising the above compound in a pharmaceutically acceptable carrier.

15 Claims, 4 Drawing Sheets

Specification includes a Sequence Listing.

(56) References Cited

U.S. PATENT DOCUMENTS

| | | | |
|---|---|---|---|
| 9,579,299 B2* | 2/2017 | Glozman | A61K 31/00 |
| 2003/0032599 A1 | 2/2003 | Lipkowski et al. | |
| 2003/0082214 A1* | 5/2003 | Williams | A61K 9/0014 |
| | | | 424/400 |
| 2003/0082225 A1* | 5/2003 | Mason | A61K 9/7053 |
| | | | 424/449 |
| 2003/0170288 A1 | 9/2003 | Carr | |
| 2004/0076648 A1* | 4/2004 | Williams | A61K 9/0014 |
| | | | 424/400 |
| 2006/0030532 A1 | 2/2006 | Lipkowski et al. | |
| 2006/0105947 A1 | 5/2006 | Carr et al. | |
| 2006/0241053 A1 | 10/2006 | Lipkowski et al. | |
| 2008/0039404 A1* | 2/2008 | Hruby | C07K 7/06 |
| | | | 514/18.3 |
| 2011/0054038 A1* | 3/2011 | Glozman | A61K 31/09 |
| | | | 514/653 |
| 2012/0310140 A1* | 12/2012 | Kramer | A61K 9/0009 |
| | | | 604/20 |
| 2014/0256709 A1* | 9/2014 | Glozman | A61K 31/00 |
| | | | 514/211.13 |
| 2016/0361378 A1* | 12/2016 | Hruby | A61K 38/08 |

FOREIGN PATENT DOCUMENTS

| | | |
|---|---|---|
| WO | WO2002102835 A2 | 12/2002 |
| WO | WO2003090697 A2 | 11/2003 |
| WO | WO2004014943 A2 | 2/2004 |
| WO | WO2005007682 A2 | 1/2005 |

OTHER PUBLICATIONS

Burgess et al. J of Cell Bio. 1990, 111:2129-2138.*
Pawson et al. 2003, Science 300:445-452.*
Alaoui-lsmaili et al., Cytokine Growth Factor Rev. 2009; 20(5-6):501-7.*
Guo et al., PNAS 2004; 101 (25):9205-10.*
Alliance of Dermorphin and Neurokinin 1 receptor antagonist derived pharmacophores for the treatment of pain. Tech Lauch Arizona Technology ID#UA15-053, The university of Arizona, retrieved from the Tech Lauch Arizona website on Apr. 8, 2019.*
Ballet et al. J. Med. Chem. 2011; 54:2467-2476.*
Millet et al. BioOga. & Med. Chem. 2002; 10:2905-2912.*
Chatterjee et al., Accounts of Chemical Res. 2008; 41:1331-1342.*
Millet et al. Bioorganic Med. Chem. 2002; 10:2905-2912.*
Bonney et al. Eur. J. Pharmacol. 2004; 488:91-99.*
Yamamoto, PhD. Dissertation (p. 66-74 of the dissertation), Dept. of Chem, Univeristy of Tokyo, Japan, published Aug. 29, 2008.*
Mollica et al. Eur. J. Med. Chem. 2013; 167-177.*
Weltrowska et al. Chem. Biol. Durg Des. 2010;75:182-188.*
Yamamoto et al. J. Med. Chem. 2008; 51:1369-1376.*
Wood et al. J. Chem. Theory Comput. 2008; 4:1788-1794.*
Nair et al. Biorganic Med. Chem. Lett. 2015;25:3716-3720.*
Agnes et al., J. Med. Chem., 2006, 49, pp. 2868-2875.
Ananthan, The AAPS Journal, 2006, 8(1) Article 14, pp. E118-E125.
Bonney et al., Eur. J. Pharmacol., 2004, 488(1-3), pp. 91-99.
Bonney, 2004, European Journal of Pharmacology, 488, 91-99.
Bouchie, BioCentury, The Bernstein Reporton BioBusiness, 2007, 15(34), p. A14 of 26.
Fantin et al., Cancer Res., 2005, 65(15), pp. 6891-6900.
Foran et al., Anesthesiology, Supp., 1999, 91(3A): A944.
Foran et al., JPET, 2000, 295(3), pp. 1142-1148.
Foran et al., PNAS, 2000, 97(13), pp. 7621-7626.
Huber et al., J. of Pharmaceutical Sci., 2003, 92(7), pp. 1377-1385.
Lee et al., J. Med. Chern., 2006, 49(5), pp. 1773-1780.
Maszczynska et al., Analgesia, 1998, 3, pp. 259-268.
Maszczynska et al., Letters in Peptide Science, 1998, 5, pp. 395-398.
Millet et al., Journal of Peptide Sci., 2001, 7, pp. 323-330.
Millet, 2002, Bioorganic and Medicinal Chemistry, 10, 2905-2912.
Misterek et al., Life Sciences, 1994, vol. 54, pp. 939-944.
Rashid et al., Endocrinology, 2004,145(6), pp. 2645-2652.
Richards et al., Eur. J. Biochem., 2003, 270, pp. 2287-2294.
Rupniaketal, Pain, 1996, 67, pp. 189-195.
Sakurada et al., Pain, 1995, 60, pp. 175-180.
Sanchez-Blazquez et al., JPET, 1993, 265(2), pp. 835-843.
Schiller, The AAPS Journal, 2005, 7(3), Article 56, pp. E560-E565.
Towler et al., Neuroscience Letters, 1998, 257, pp. 5-8.
Weltrowska et al., J. Peptide Res., 2004, 63, pp. 63-68.

* cited by examiner

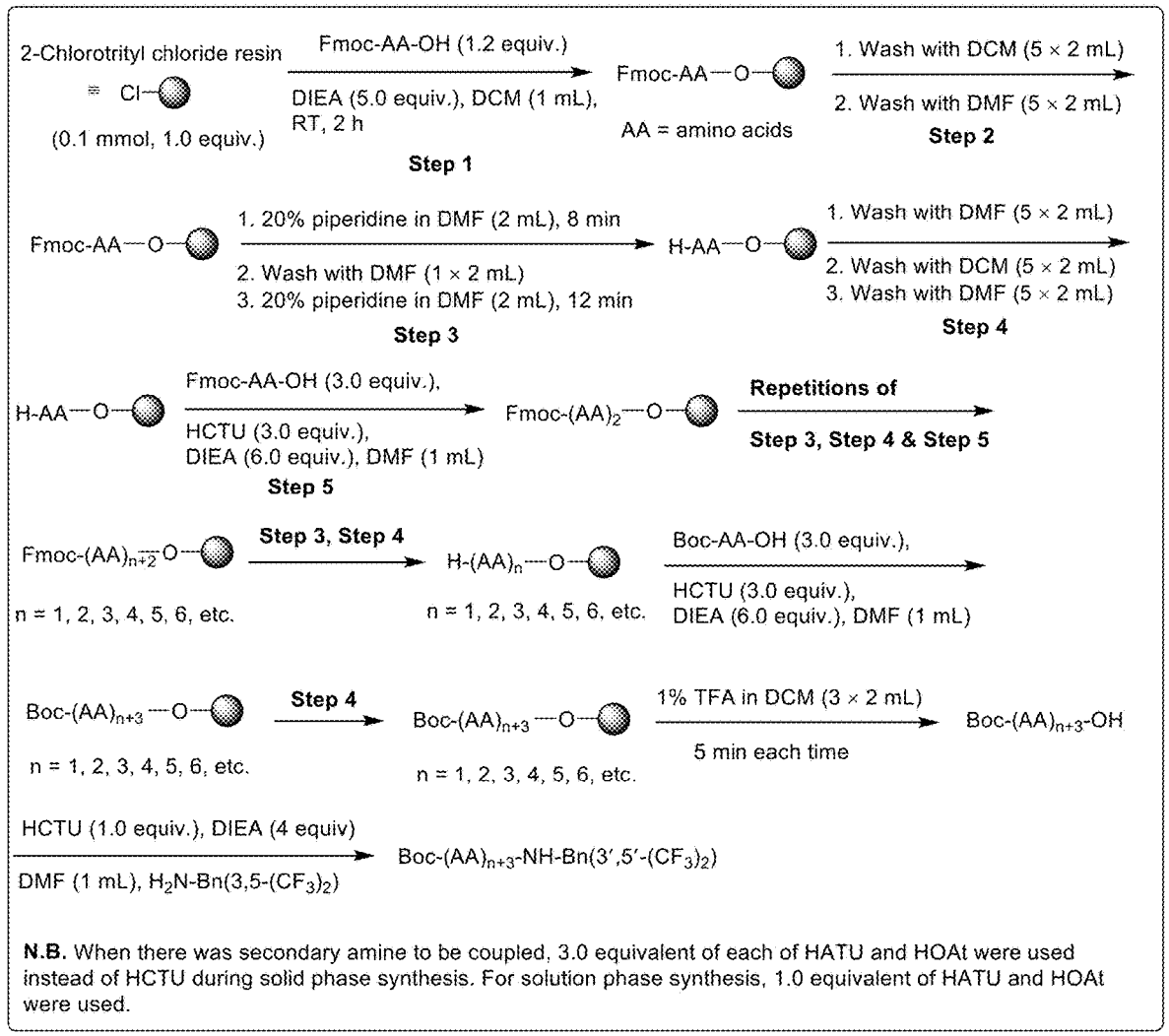
Fig. 1 – Prior Art
General path for the synthesis of multivalent/multifunctional ligands

*Fmoc-deprotection followed by*
o-NBS Protection (for 0.1 mmol resin bound primary amine)
1. o-NBS-Cl (4.0 equiv) in 1.0 mL NMP
2. *sym*-Collidine (10.0 equiv.)
3. Mix with resin and stirr for 15 min,
4. Filter the resin and wash with NMP (1 ⨯ 1 min)
5. Repeat 1-2 and stirr for 10 min,
6. Filter and wash the resin (5 ⨯ 1 min)

N-methylation
DBU-mediated method; for all except Cys, His and their analogs, Time 20 min
1. DBU (3.0 equiv.) in 1.0 mL NMP
2. Treat the resin with DBU soln for 3 min
3. Add DMS (10.0 equiv.) in 0.5 mL NMP
4. Treat the resin with the DMS solution for 2 min,
5. Filter the resin and wash with NMP (1 ⨯ min)
6. Repeat 1-4, 7. Filter and wash the resin with NMP (5 ⨯ 1 min)

Mitsunubu reaction-mediated method; for all amino acids, Time 50 min
1. Rinse the resin with anhy THF (1.0 mL, 2 ⨯ 2 min)
2. Ph$_3$P (5 equiv.) in 0.5 mL anhy. THF
3. Add 10 equiv. of MeOH to the soln and mix well
4. Treat the resin with the soln for 2 min
5. Prepare a soln of DIAD (5.0 equiv.) in in 0.5 mL anhy.THF
6. Divide the soln made in step 5 into 5 equal parts and add to the mixture of step 4 and stirr for 10 min after each addition (this step is highly exothermic)
7. Filter and wash with anhy THF (1 ⨯ 1 min) with stirring
8. Repeat 1-6
9. Wash the resin with anhy THF (5 ⨯ 1 min)

o-NBS deprotection
1. 2-mercatoethanol (10.0 equiv.) and DBU (5.0 equiv) in 1.0 mL of NMP
2. Treat the resin with the soln for 5 min,
3. Filter and wash the resin with NMP (1 ⨯ 1 min)
4. Repeat steps 1-2 and filter the resin,
5. Wash the resin with NMP (5 ⨯ 1 min)

Fig. 2 – Prior Art

Steps for *N*-methylation on solid phase

Paw withdrawal latency after i.t. administration of ligand 3 (AKG115)

Tail Flick latency after i.t. administration of ligand AKG127

Percentage of antinociception calculated at the same dose of ligands 3 and 5

BIFUNCTIONAL COMPOUNDS FOR RELIEF OF PAIN COMPRISING AN OPIOID RECEPTOR AGONIST MOIETY AND A NK1 RECEPTOR ANTAGONIST MOIETY AND METHODS FOR TREATING PAIN

STATEMENT REGARDING FEDERALLY FUNDED RESEARCH

This invention was made with government support under Grant Nos. P01 DA006284 and R01 DA013449 awarded by NIH. The government has certain rights in the invention.

BACKGROUND OF THE INVENTION

The present invention relates generally to methods and compounds for the treatment of pain, more specifically compounds, compositions comprising the compounds, and methods for acute and chronic pain relief and acute and chronic intervention for drug abuse.

Pain is caused by a highly complex perception of an aversive or unpleasant sensation, and the management of pain, mainly sustained and neuropathic pain, is a major challenge as millions of people all over the world suffer from such kind of pain every day. Opioids continue to be the backbone for the treatment of these pain states. However, constant opioid treatment is accompanied with serious undesirable effects including drowsiness and mental clouding, nausea and emesis, constipation and in many cases dependence and addiction. Continuous use of opioid therapy also develops analgesic tolerance and hyperalgesia in many patients. These unwanted effects significantly diminish the patients' quality of life. The mechanisms for these side effects are still largely unclear. Sustained pain states lead to neuroplastic modifications in both ascending and descending pathways in the spinal column in which there is both an augmented release of neurotransmitters (e.g., substance P) that intensify pain and increased expression of the corresponding receptors responsible for releasing those pain-promoting ligands. Currently used drugs for the management of prolonged and neuropathic pain mostly can only control pain and cannot neutralize against these induced neuroplastic modifications. Thus, it is found that the drugs currently in use as analgesic cannot work well in these pathological conditions.

Opioid drugs also are widely used following major surgery and to control pain of terminal diseases such as cancer, but its use is limited by several undesired side effects including nausea, vomiting, constipation, dizziness, system changes (neuroplasticity) due to prolonged pain or treatment by the opioid drugs and the development of tolerance and physical dependence, which mainly come through the µ opioid receptor [1, 2, 3], Because of these limitations the search for the novel type of analgesics which have strong pain controlling effect without development of tolerance and/or physical dependence has been performed for decades [4].

Opiates work in the brain at specific "opiate receptors." Several types of the opiate receptors are known, but the main receptor for pain is called the µ receptor. Administering receptor agonists can cause full or partial stimulation or effect at the receptor, while administering antagonists blocks the effect of the receptor. It is widely accepted that a µ receptor agonist such as morphine has higher antinociceptive activity accompanied with high abuse liability. On the other hand, the activation of the δ opioid receptor has lower analgesic efficacy, but has reduced addictive potential [5], It is also generally known that the selective agonists at the δ opioid receptor have analgesic activity in numerous animal models with fewer adverse effects, though their efficacy is less potent than that of their widely-used µ counterparts[1, 2, 3], Thus, selective δ opioid agonists with enhanced analgesic activity are expected as a potent drug candidate for severe pain control.

Substance P is the preferred ligand for the neurokinin 1 (NK1) receptor and is known to contribute to chronic inflammatory pain and participate in central sensitization and associated hyperalgesia. In the pain states, substance P, which is an 11-amino acid polypeptide, is known as a major neurotransmitter of pain signals as well as the signals induced by opioid stimulation [1, 2, 3], Substance P and NK1 receptor expression increases after sustained opioid administration. Also, repeated morphine exposure results in enhanced levels of substance P in pain pathways both in vitro and in vivo, which could induce increased pain; increased pain could require increased pain-relief and thus be manifested as "antinociceptive tolerance" [6], Interestingly, co-administration of δ/µ opioid agonists and a substance P antagonist showed enhanced antinociceptive effect in acute pain states, and in prevention of opioid-induced tolerance in chronic trials. These results suggest that the signals through opioid receptors and neurokinin 1 (NK1) receptors are not independent, but have strong and critical interaction. Moreover, the mice lacking NK1 receptors, the preferred receptor of substance P, didn't show rewarding properties for opiates [1].

According to these observations, the use of multimodal combination analgesic therapies or therapies with a single molecule possessing the ability to interact with multiple analgesic targets has become attractive [7, 8]. Advantages of hybrid compounds system are developing bioactive compounds designed with a broad spectrum of receptor affinities and single administration of a chimeric compound instead of a specific ratio of two different compounds.

Many classes of C-terminal modified compounds have been considered by investigators, and a number of approaches to modifying the C-terminal have been reported [9, 10, 11], These approaches can be classified into many categories including nucleophilic cleavage of protected compounds bound from appropriate resins, attachment with a C-terminal functional group, side chain anchoring followed by normal solid phase N-to-C peptide synthesis, backbone amide attachment onto a solid support, inverse C-to-N solid phase biopolymer synthesis, and conventional solution phase synthesis[10]. However, it is difficult to synthesize C-terminal esters or tertiary amides by the first two methods, and designed compounds didn't have a suitable side chain moiety to anchor on a resin. Repeated inverse C-to-N coupling leads to severe racemization, and conventional Boc solution phase compound synthesis is very labor intensive for large amounts of longer compounds.

The importance of interactions between biologically active compounds and membrane has become increasingly appreciated recently. The strong influence of these interactions on ligand activity, membrane permeability and toxicity has been increasingly clarified [12], Among these compounds, peptides function as transmitters of many unique and diverse biological signals which largely depend on their amino acid sequence, and their interactions with membrane localized receptor/acceptors. However, the signal transduction of compounds is made not by the primary sequence but by higher order dynamic three-dimensional conformations. Therefore, the changes in 3D structure and dynamics which are induced by the modification of primary sequence have been a long-term interest, since 3D structure and the dynamics have an influence on the biological properties. In fact, many G-protein coupled receptors (GPCRs), which are the typical membrane-bound proteins, generally have their ligand binding site in the hydrophobic trans-membrane (TM) domains[13, 14, 15, 16], Compound-membrane interaction also is very important when a compound penetrates membranes, such as the blood brain barrier[12, 17], Hence, understanding of the membrane-bound structures of compounds and compound-membrane interactions is indispensable to obtain further insight into their diverse biological behaviors.

The foregoing discussion of the prior art derives primarily from U.S. Pat. No. 8,026,218 to Hruby et al., one of the co-inventors, in which there are disclosed certain novel chimeric compounds comprising an agonist opioid receptor binding moiety at its N-terminus and an antagonist neurokinin-1 (NK1) receptor binding moiety at its C-terminus for producing analgesia, a pharmaceutical composition comprising the chimeric compound, a method of making the compound, and a method of treating pain using the novel chimeric compounds.

While prior art opioid-based compounds, such as described above and in the aforesaid U.S. Pat. No. 8,016,218 are proving useful in treatment of pain, constant opioid treatment often is accompanied with serious undesirable effects including drowsiness and mental clouding, nausea and emesis, and constipation. Continuous use of opioid therapy also develops analgesic tolerance and hyperalgesia in many patients. These unwanted effects significantly diminish the patients' quality of life. The mechanisms for these side effects are still largely unclear. Sustained pain states lead to neuroplastic modifications in both ascending and descending pathways in the spinal column in which there is both an augmented release of neurotransmitters (e.g., substance P) that intensify pain and increased expression of the corresponding receptors responsible for releasing those pain-promoting ligands. Currently used drugs for the management of prolonged and neuropathic pain mostly can only control pain and cannot neutralize against these induced neuroplastic modifications. Thus, drugs currently in use as analgesic cannot work well in these pathological conditions.

We have found that agonist activities at Mu-type and Delta-type opioid receptors (MOR and DOR), and antagonist activity at NKI is beneficiary over targeting a single receptor. This combination addresses several fundamental biological effects such as enhanced potency in acute pain models and inhibition of opioid-induced tolerance in chronic tests using rats. A study revealed that NK1 knockout mice did not show the rewarding properties of morphine. Thus, the combination of opioid receptor agonist and NK1 receptor antagonist activity may have synergistic effects in the management of prolonged pain states that involve higher substance P activity. Drug combinations have restrictions as therapeutics because of poor patient compliance, difficulties in drug metabolism, distribution, and possible drug-drug interactions. Our invention focuses on combining these two or three different activities in one ligand which has appropriate metabolic and pharmacological properties. The ligand has potent analgesic affects not only in acute pain but also in prolonged and neuropathic pain states without the development of unwanted side effects. However, prior to our investigation, it was still largely unclear what binding ratio(s) for the receptors should be ideal to achieve our desired biological profile. To address these highly challenging issues an innovative approach has been taken to design, synthesize and evaluate the detail biological profile of the ligands showing different kind of ratios of binding affinity for all three receptors with appropriate functional activities. It might be the case that one particular ligand cannot satisfy the all requirements. The present invention employs an innovative approach to design, synthesize and evaluate the detail biological profile of the ligands showing different kind of ratios of binding affinity for all three receptors with appropriate functional activities.

The present approach of our drug-design is based on adjacent and overlapping pharmacophores, in which an opioid agonist pharmacophore is placed at the N-terminus and the NK1 antagonist pharmacophore sits at the C-terminus of a single peptide derived ligand. The opioid pharmacophore of these multivalent/multifunctional ligands were designed based on the sequences of well-known opioid agonist ligands including enkephalin (Met-enkephalin: H-Tyr-Gly-Gly-Phe-Met (SEQ ID NO: 1) and Leu-Enkephalin: H-Tyr-Gly-Gly-Phe-Leu (SEQ ID NO:2)), DAMGO, (H-Tyr-D-Ala-Gly-N-MePhe-Gly-OH (SEQ ID NO:3)), dermorphin (H-Tyr-D-Ala-Phe-Gly-Tyr-Pro-Ser-NH$_2$ (SEQ ID NO:4)), morphiceptin (H-Tyr-Pro-Phe-Pro-NH$_2$ (SEQ ID NO:5)), and endomorphins (Endomorphin 1: H-Tyr-Pro-Trp-Phe-NH$_2$ (SEQ ID NO:6); Endomorphin 2: H-Tyr-Pro-Phe-Phe-NH$_2$ (SEQ ID NO:7)), while the NK1 antagonist pharmacophore (i.e. -Pro-Leu-Trp-NH-Bn(3',5'-(CF$_3$)$_2$))) was adopted from the previously published pharmacophore (e.g., TY027: H-Tyr-D-Ala-Gly-Phe-Met-Pro-Leu-Trp-NH-Bn(3',5'-(CF$_3$)$_2$) (SEQ ID NO:8)) (Hruby et al. U.S. Pat. No. 8,026,218) for the same kind of activity. The two pharmacophores are joined directly or by a linker, which might be working as an address region for both pharmacophores as well as a spacer between them. It should be highlighted that the designed multivalent/multifunctional ligands have additional rewards over a cocktail of individual drugs for easy administration, a simple ADME property and no drug-drug interactions. Local concentration is also expected to be higher than that in the coadministration of drug cocktails as the expression of the NK1 and opioid receptors as well as the neurotransmitters show a significant degree of overlap in the central nervous system, resulting to synergies in potency and efficacy. Previous studies have shown that the lead bifunctional compounds, TY005 (H-Tyr'-D-Ala$^2$-Gly$^3$-Phe$^4$-Met$^5$-Pro$^6$-Leu$^7$-Trp$^8$-O-NH-Bn(3',5'-(CF$_3$)$_2$ (SEQ ID NO:9)) and TY027 (H-Tyr$^1$-D-Ala$^2$ Gly$^3$-Phe$^4$-Met$^5$-Pro$^6$-Leu$^7$-Trp$^8$-NH-Bn(3',5'-(CF$_3$)$_2$ (SEQ ID NO:8)) are capable to treat neuropathic pain in a rodent model with blood brain barrier permeability, no development of opioid-induce tolerance, and no development of reward liability, supporting our hypothesis that a single ligand containing opioid agonist/NK1 antagonist activities is effective against neuropathic pain[18]. It should be noted here that the above mentioned ligands have shown their binding affinity and functional activity on both DOR and MOR, but with some selectivity for the former one over the latter one while maintaining their biological profile at the NK1 receptor. Surprisingly, we have found that combining two activities, i.e. opioid agonists and NK1 antagonist, on one ligand provides enhanced metabolic and pharmacological properties including increased blood-brain barrier penetration not observed when an opioid agonists and an NK1 antagonist are administered separately.

More particularly, we have shown that agonist activities at Mu-type and Delta-type opioid receptors (MOR and DOR), and antagonist activity at NKI is beneficiary over targeting a single receptor. This combination explains several fundamental biological effects such as enhanced potency in acute pain models and inhibition of opioid-induced tolerance in chronic tests using rats. A study revealed that NK1 knockout mice did not show the rewarding properties of morphine. Thus, the combination of opioid receptor agonist and NK1 receptor antagonist activity may have synergistic effects in the management of prolonged pain states that involve higher substance P activity. Drug combinations have restrictions as therapeutics because of poor patient compliance, difficulties in drug metabolism, distribution, and possible drug-drug interactions. Our new approach focuses on combining these two or three different activities in one ligand which should have appropriate metabolic and pharmacological properties. The ligand would have potent analgesic affects not only in acute pain but also in prolonged and neuropathic pain states without the development of unwanted side effects. But it is still largely unclear what binding ratio(s) for the receptors should be ideal to achieve our desired biological profile. To address these highly challenging issues an innovative approach has been taken to design, synthesize and evaluate the detail biological profile of the ligands showing different kind of ratios of binding affinity for all three receptors with appropriate functional activities. It might be the case that one particular ligand cannot satisfy the all requirements. The present invention employs an innovative approach to design, synthesize and evaluate the detail biological profile of the ligands showing different kind of ratios of binding affinity for all three receptors with appropriate functional activities.

The present approach of our drug-design is based on adjacent and overlapping pharmacophores, in which an opioid agonist pharmacophore is placed at the N-terminus and the NK1 antagonist pharmacophore sits at the C-terminus of a single peptide derived ligand. The opioid pharmacophore of these multivalent/multifunctional ligands were designed based on the sequences of well-known opioid agonist ligands including enkephalin (Met-enkephalin: Tyr-Gly-Gly-Phe-Met (SEQ ID NO: 1) and Leu-Enkephalin: Tyr-Gly-Gly-Phe-Leu (SEQ ID NO:2)), DAMGO, (H-Tyr-D-Ala-Gly-NMePhe-Gly-OH (SEQ ID NO:3)), dermorphin (H-Tyr-D-Ala-Phe-Gly-Tyr-Pro-Ser-NH$_2$ (SEQ ID NO:4)), morphiceptin (H-Tyr-Pro-Phe-Pro-NH$_2$ (SEQ ID NO:5)), and endomorphins (Endomorphin 1: H-Tyr-Pro-Trp-Phe-NH$_2$ (SEQ ID NO:6); Endomorphin 2: H-Tyr-Pro-Phe-Phe-NH$_2$ (SEQ ID NO:7)), while the NK1 antagonist pharmacophore (i.e. -Pro-Leu-Trp-NH-Bn(3',5'-(CF$_3$)$_2$))) was adopted from the previously published pharmacophore (e.g., TY027: H-Tyr-D-Ala-Gly-Phe-Met-Pro-Leu-Trp-NH-Bn (3',5'-(CF$_3$)$_2$) (SEQ ID NO: 8)) for the same kind of activity. The two pharmacophores are joined directly or by a linker, which might be working as an address region for both pharmacophores as well as a linker between them. It should be highlighted that the designed multivalent/multifunctional ligands have additional rewards over a cocktail of individual drugs for easy administration, a simple ADME property and no drug-drug interaction. Local concentration is also expected to be higher than that in the coadministration of drug cocktails as the expression of the NK1 and opioid receptors as well as the neurotransmitters show a significant degree of overlap in the central nervous system, resulting to synergies in potency and efficacy. Previous studies have shown that the lead bifunctional compounds, TY005 (H-Tyr$^1$-D-Ala$^2$-Gly$^3$-Phe$^4$-Met$^5$-Pro$^6$-Leu$^7$-Trp$^8$-O—NH-Bn(3',5'-(CF$_3$)$_2$) (SEQ ID NO:9)) and TY027 (H-Tyr$^1$-D-Ala$^2$-Gly$^3$-Phe$^4$-Met$^5$-Pro$^6$-Leu$^7$-Trp$^8$-NH-Bn(3',5'-(CF$_3$)$_2$ (SEQ ID NO:8)) are capable to treat neuropathic pain in a rodent model with blood brain barrier permeability, no development of opioid-induce tolerance, and no development of reward liability, supporting our hypothesis that a single ligand containing opioid agonist/NK1 antagonist activities is effective against neuropathic pain. It should be noted here that the above mentioned ligands have shown their binding affinity and functional activity on both DOR and MOR, but with some selectivity for the former one over the latter one while maintaining their biological profile at NK1 receptor. Surprisingly, we have found that combining two activities, i.e. opioid agonists and NK1 antagonist, on one ligand provides enhanced metabolic and pharmacological properties including increased blood-brain barrier penetration not observed when an opioid agonists and an NK1 antagonist are administered separately.

In one aspect of the invention, there is provided a compound for treatment of pain comprising a single multivalent/multifunctional ligand with agonist activity at opioid receptors and with antagonist activity at NK1 receptors, joined by a linker, or by a covalent bond. In such aspect opioid pharmacophore moiety preferably is selected from the group consisting DAMGO, dermorphin, morphiceptin, and endomorphin, and/or the linker preferably has a length of one to three amino acids.

In one aspect of the invention, the opioid pharmacophore moiety is cyclic.

In another aspect of the invention, the compound has the structure:

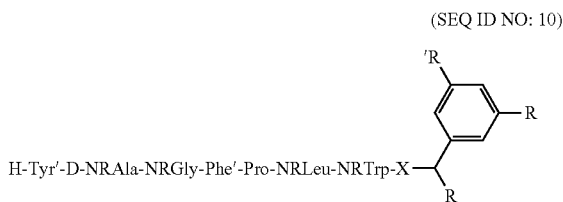

(SEQ ID NO: 10)

Tyr'=Tyr and its derivatives, e.g., Dmt etc.; Phe'=Phe and its derivatives, e.g., NMePhe, Phe(4-F) etc.; R=H, Me, etc.; R'=H, CH$_3$, CF$_3$ etc.; X=NH, NMe, etc.

or an analog thereof selected from the group consisting of: H-Tyr-D-Ala-Gly-NMePhe-Pro-Leu-Trp-NH-Bn(3',5'-(CF$_3$)$_2$) (SEQ ID NO: 11); H-Dmt-D-Ala-Gly-NMePhe-Pro-Leu-Trp-NH-Bn(3',5'-(CF$_3$)$_2$) (SEQ ID NO: 12); H-Dmt-D-Ala-Gly-Phe-Pro-Leu-Trp-NH-Bn(3',5'-(CF$_3$)$_2$) (SEQ ID NO: 13); H-Dmt-D-Ala-Gly-Phe(4-F)-Pro-Leu-Trp-NH-Bn(3',5'-(CF$_3$)$_2$) (SEQ ID NO: 14); H-Dmt-D-Ala-Gly-NMePhe(4-F)-Pro-Feu-Trp-NH-Bn(3',5'-(CF$_3$)$_2$) (SEQ ID NO: 15); H-Dmt-D-Ala-Gly-Phe(4-Cl)-Pro-Leu-Trp-NH-Bn(3',5'-(CF$_3$)$_2$) (SEQ ID NO: 16); H-Dmt-D-Ala-Gly-Phe(4-Br)-Pro-Leu-Trp-NH-Bn(3',5'-(CF$_3$)$_2$) (SEQ ID NO: 17); and H-Dmt-D-Ala-Gly-Phe(4-I)-Pro-Leu-Trp-NH-Bn (3',5'-(CF$_3$)$_2$) (SEQ ID NO: 18).

In another aspect of the invention the compound has the structure:

(SEQ ID NO: 19)

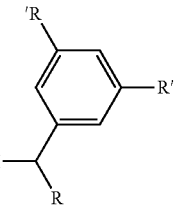

H-Tyr'-D-NRAla-NRGly-Phe'-(AA)ₓ-Pro-NRLeu-NRTrp-X— x = 1, 2, 3 etc.

Tyr'=Tyr and its derivatives, e.g., Dmt etc.; Phe'=Phe and its derivatives, e.g., NMePhe, Phe(4-F) etc.; R=H, Me, etc.; AA=natural/unnatural amino acid e.g., Nle, Gly, β-Ala, γ-Abu, Ahx, 4-Amb, 4-Abz, 4-Apac, 4-Ampa etc.; R'=H, CH₃, CF₃ etc.; X=NH, NMe, etc.

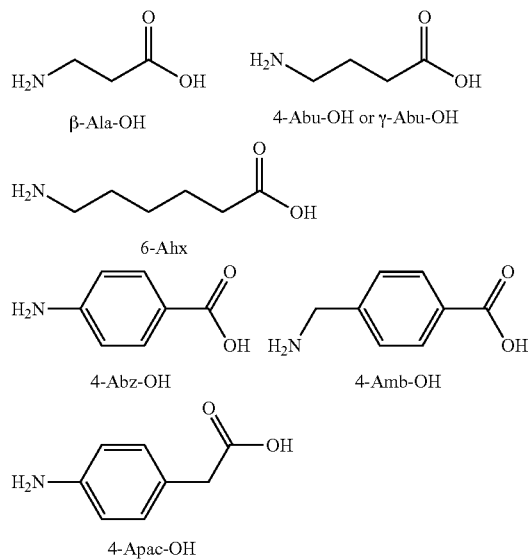

β-Ala-OH

4-Abu-OH or γ-Abu-OH

6-Ahx

4-Abz-OH    4-Amb-OH

4-Apac-OH

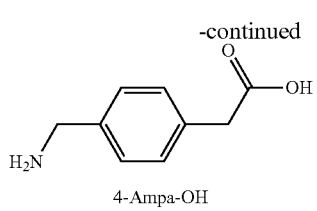

4-Ampa-OH and an analog thereof selected from the group consisting of: H-Tyr-D-Ala-Gly-NMePhe-Nle-Pro-Leu-Trp-NH-Bn(3',5'-(CF₃)₂) (SEQ ID NO:20); H-Tyr-D-Ala-Gly-NMePhe-Gly-Pro-Leu-Trp-NH-Bn(3',5'-(CF₃)₂) (SEQ ID NO:21); H-Tyr-D-Ala-Gly-Phe(4-F)-Gly-Pro-Leu-Trp-NH-Bn(3',5'-(CF₃)₂) (SEQ ID NO:22); H-Tyr-D-Ala-Gly-NMePhe(4-F)-Gly-Pro-Leu-Trp-NH-Bn(3',5'-(CF₃)₂) (SEQ ID NO:23); H-Tyr-D-Ala-Gly-NMePhe-β-Ala-Pro-Leu-Trp-NH-Bn(3',5'-(CF₃)₂) (SEQ ID NO:24); H-Tyr-D-Ala-Gly-NMePhe-γ-Abu-Pro-Leu-Trp-NH-Bn(3',5'-(CF₃)₂) (SEQ ID NO:25); H-Tyr-D-Ala-Gly-NMePhe-[[4]]6-Ahx-Pro-Leu-Trp-NH-Bn(3',5'-(CF₃)₂) (SEQ ID NO:26); H-Tyr-D-Ala-Gly-NMePhe-4-Amb-Pro-Leu-Trp-NH-Bn(3',5'-(CF₃)₂) (SEQ ID NO:27); H-Tyr-D-Ala-Gly-NMePhe-4-Abz-Pro-Leu-Trp-NH-Bn(3',5'-(CF₃)₂) (SEQ ID NO:28); H-Tyr-D-Ala-Gly-NMePhe-4-Apac-Pro-Leu-Trp-NH-Bn(3',5'-(CF₃)₂) (SEQ ID NO:29); and H-Tyr-D-Ala-Gly-NMePhe-4-Ampa-Pro-Leu-Trp-NH-Bn(3',5'-(CF₃)₂) (SEQ ID NO:30).

In still yet another aspect of the invention, the compound has the structure:

(SEQ ID NO:31)

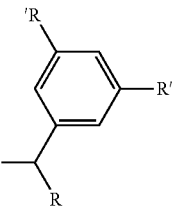

H-Tyr'-D-NRAla-NRGly-Phe'-(AA)ₓ-Pro-NRLeu-NRTrp-X— x = 1, 2, 3 etc.

Tyr'=Tyr or its derivative, e.g., Dmt etc.; Phe'=Phe or its derivative, e.g., NMePhe, Phe(4-F), NMePhe(4-F), etc.; R=H, Me, etc.; AA=natural/unnatural amino acid e.g., Ser, D-Ser, Homo-Ser, Lys, Om, Dab, Dap, Ser-4-Apac, Asn, D-Asn, Gin, D-Gln, Gln-4-Apac, etc.; R'=H, CH₃, CF₃ etc.; X=NH, NMe, etc.

or an analog thereof selected from: SEQ ID NO:31, where
Tyr'=Tyr, R=H, Phe'=Phe, x=1, AA=Ser; X=NH, R'=CF₃;
Tyr'=Tyr, R=H, Phe'=Phe, x=1, AA=Homo-Ser; X=NH, R'=—CF₃;
Tyr'=Tyr, R=H, Phe'=Phe, x=1, AA=Ser; X=NH, R'=CF₃;
Tyr'=Tyr, R=H, Phe'=NMePhe, x=1, AA=Ser; X=NH, R'=—CF₃;
Tyr'=Dmt, R=H, Phe'=NMePhe, x=1, AA=Ser; X=NH, R'=—CF₃;
Tyr'=Tyr, R=H, Phe'=Phe(4-F), x=1, AA=Ser; X=NH, R'=—CF₃;
Tyr'=Tyr, R=H, Phe'=NMePhe(4-F), x=1, AA=Ser; X=NH, R'=—CF₃;
Tyr'=Dmt, R=H, Phe'=NMePhe(4-F), x=1, AA=Ser; X=NH, R'=—CF₃;
Tyr'=Tyr, R=H, Phe'=NMePhe, x=2, (AA)x=Ser-Gly; X=NH, R'=—CF₃;
Tyr'=Dmt, R=H, Phe'=NMePhe, x=2, (AA)x=Ser-Gly; X=NH, R'=—CF₃;
Tyr'=Tyr, R=H, Phe'=Phe, x=1, AA=Asn; X=NH, R'=—CF₃;
Tyr'=Tyr, R=H, Phe'=Phe, x=1, AA=D-Asn; X=NH, R'=—CF₃;
Tyr'=Tyr, R=H, Phe'=Phe, x=1, AA=Gln; X=NH, R'=—CF₃;
Tyr'=Tyr, R=H, Phe'=Phe, x=1, AA=D-Gln; X=NH, R'=—CF₃;
Tyr'=Tyr, R=H, Phe'=NMePhe, x=1, AA=Gln; X=NH, R'=—CF₃;
Tyr'=Dmt, R=H, Phe'=NMePhe, x=1, AA=Gln; X=NH, R'=—CF₃;
Tyr'=Tyr, R=H, Phe'=Phe(4-F), x=1, AA=Gln; X=NH, R'=—CF₃;
Tyr'=Tyr, R=H, Phe'=NMePhe(4-F), x=1, AA=Gln; X=NH, R'=—CF₃;
Tyr'=Dmt, R=H, Phe'=NMePhe(4-F), x=1, AA=Gln; X=NH, R'=CF₃;
Tyr'=Tyr, R=H, Phe'=NMePhe, x=2, (AA)x=Gln-Gly; X=NH, R'=CF₃;
Tyr'=Dmt, R=H, Phe'=NMePhe, x=2, (AA)x=Gln-Gly; X=NH, R'=—CF₃.

In still yet another aspect of the invention the compound has the structure:

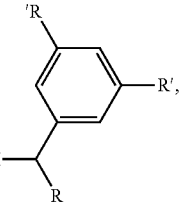

(SEQ ID NO:32)

H-Tyr'-D-NRAla-Phe'-NRGly-(AA)$_x$-Pro-NRLeu-NRTrp-X— x = 0, 1, 2, 3 etc.

Tyr'=Tyr and its derivatives, e.g., Dmt etc.; Phe'=Phe and its derivatives, e.g., NMePhe, Phe(4-F), etc.; R=H, Me, etc.; AA=natural/unnatural amino acid, e.g., 4-Amb, 4-Apac, Lys, etc.; X=NH, NMe, etc.; R'=H, CH₃, CF₃ etc.

Exemplary compounds of SEQ ID NO:32 include compounds where (i) R=H, Phe'=Phe, Tyr'=Tyr, x=0, X=NH, R'=CF₃; (ii) R=H, Phe'=Phe, Tyr'=Tyr, x=0, X=NMe, R'=CF₃; (iii) R=H, Phe'=Phe, first Tyr'=Dmt, second Tyr'=Tyr, x=0, X=NH, R'=CF₃; (iv) R=H, Phe'=Phe(p-F), Tyr'=Tyr, x=0, X=NH, R'=CF₃; and (v) R=H, Phe'=Phe(p-F), first Tyr'=Dmr, second Tyr'=Tyr, x=0, X=NH, R'=CF₃.

In a further aspect of the invention the compound has the structure:

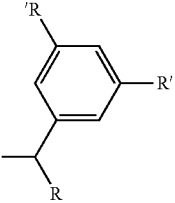

(SEQ ID NO:33)

H-Tyr'-Pro-NRGly-Phe'-Tyr'-(AA)$_x$-NRLeu-NRTrp-X— x = 1, 2, 3 etc.

where Tyr'=Tyr or its derivative e.g., Dmt etc.; Phe'=Phe or its derivative, e.g., NMePhe, Phe(4-F) etc.; R=H, Me etc.; AA=natural/unnatural amino acid e.g., AA=4-Amb, 4-Apac, Lys, etc.; X=Nh, Nme etc., or an analog thereof selected from H-Tyr-Pro-Phe-Pro-Leu-Trp-NH-Bn(3',5'-(CF$_3$)$_2$) (SEQ ID NO:34); H-Tyr-Pro-Phe-Pro-Pro-Leu-Trp-NH-Bn (3',5'-(CF$_3$)$_2$) (SEQ ID NO:35); H-Tyr-Pro-Phe-Gly-Nle-Pro-Leu-Trp-NH-Bn(3',5'-(CF$_3$)$_2$) (SEQ ID NO:36); H-Tyr-Pro-Phe-Pro-4-Amb-Pro-Leu-Trp-NH-Bn(3',5'-(CF$_3$)$_2$) (SEQ ID NO:37); H-Tyr-Pro-Phe-Pro-4-Ampa-Pro-Leu-Trp-NH-Bn(3',5'-(CF$_3$)$_2$) (SEQ ID NO:38); H-Tyr-Pro-Phe-Gly-Pro-Leu-Trp-NH-Bn(3',5'-(CF$_3$)$_2$) (SEQ ID NO:39); H-Tyr-Pro-Phe-NMeGly-Pro-Leu-Trp-NH-Bn(3',5'-(CF$_3$)$_2$) (SEQ ID NO:40); H-Tyr-Pro-Gly-Phe-Pro-Leu-Trp-NH-Bn (3',5'-(CF$_3$)$_2$) (SEQ ID NO:41); H-Tyr-Pro-Gly-NMePhe-Pro-Leu-Trp-NH-Bn(3',5'-(CF$_3$)$_2$) (SEQ ID NO:42).

In a further aspect of the invention the compound has the structure:

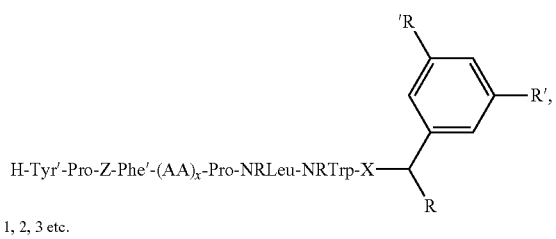

H-Tyr'-Pro-Z-Phe'-(AA)$_x$-Pro-NRLeu-NRTrp-X x = 0, 1, 2, 3 etc.

(SEQ ID NO:43)

where Tyr'=Tyr or its derivative, e.g., Dmt etc.; Z=Phe' or Trp' or absent; Trp'=Trp or its derivative, e.g., NMeTrp etc.; Phe'=Phe or its derivative, e.g., NMePhe, Phe(4-F) etc.; R=H, Me etc.; AA=natural/unnatural amino acid., e.g., AA=4-Amb, 4-Apac, Lys, etc.; X=NH, NMe etc., or an analog thereof selected from: H-Tyr-Pro-Trp-Phe-Pro-Leu-Trp-NH-Bn(3',5'-(CF$_3$)$_2$) (SEQ ID NO:44); H-Tyr-Pro-Phe-Phe-Pro-Leu-Trp-NH-Bn(3',5'-(CF$_3$)$_2$) (SEQ ID NO:45); H-Tyr-Pro-Trp-NMePhe-Pro-Leu-Trp-NH-Bn(3',5'-(CF$_3$)$_2$) (SEQ ID NO:46); H-Tyr-Pro-Phe-NMePhe-Pro-Leu-Trp-NH-Bn(3',5'-(CF$_3$)$_2$) (SEQ ID NO:47); H-Tyr-Pro-NMeTrp-NMePhe-Pro-Leu-Trp-NH-Bn(3',5'-(CF$_3$)$_2$) (SEQ ID NO:48); H-Tyr-Pro-NMePhe-NMePhe-Pro-Leu-Trp-NH-Bn(3',5'-(CF$_3$)$_2$) (SEQ ID NO:49); H-Tyr-D-Ala-Gly-Phe-Pro-Leu-Trp-NMe-Bn(3',5'-(CF$_3$)$_2$) (SEQ ID NO:50); H-Tyr-D-Ala-Phe-Pro-Leu-Trp-NMe-Bn(3',5'-(CF$_3$)$_2$) (SEQ ID NO:51).

The invention also provides a pharmaceutical composition comprising the compound as above described in a pharmaceutical-acceptable carrier.

The invention also provides a method for treating pain which comprises administering an effective amount of the above described composition to an individual in need of treatment, as needed, preferably in a dose range of 1 mg/Kg to 100 mg/Kg.

The invention also provides a method for forming compound as above described, comprising the steps of solid phase peptide synthesis, cyclization via coupling of appropriate functional groups on solid phase, C-terminal modification and removal of all protecting group in solution phase.

Further features and advantages of the present invention are seen from the following detailed description taken in conjunction with the accompanying drawings, wherein;

FIG. 1 illustrates a general path for the synthesis of multivalent/multifunctional ligands useful in accordance with the present invention;

FIG. 2 illustrates steps for N-methylation on solid phase useful in accordance with the present invention;

Figure 3:
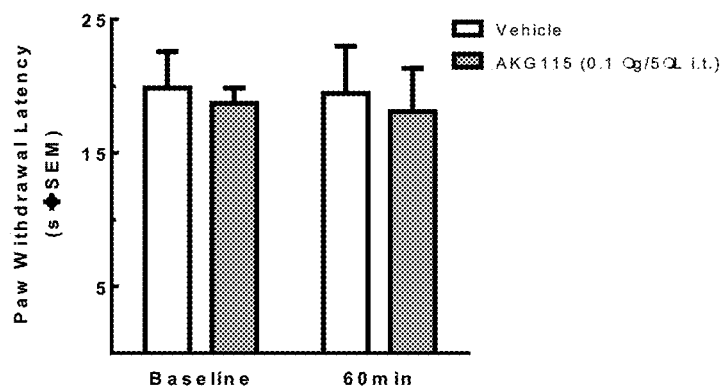
FIG. 3 shows structures of two potent opioid ligands in accordance with the present invention.

There is no human being in the entire world that has not faced some kind of pain at some point of time in her/his life. It is essential for our survival. According to the International Association for the Study of Pain (IASP), pain is defined as "an unpleasant sensory and emotional experience associated with actual or potential tissue damage or described in terms of such damage" [19], Pain can be classified in numerous ways and accordingly, different types of pain are discussed in the literature. Pain has significant physical, economic and social impact. Approximately 1.5 billion people around the globe suffer from chronic pain [20], The costs associated with pain treatment are much higher than that involved for the treatment of heart disease or cancer [21], Generally, acute pain associated with accidental injury or surgery is cured. But nearly 50% of patients who have gone through surgery face chronic pain [22]. Under-treatment of postsurgical acute pain has been found as a major reason for moderate to severe or even extreme pain in two thirds of these patients [23], Support in favor of these statements comes from the observations made during the study on effective treatment of patients with acute pain [24, 25].

In spite of having many serious side effects including respiratory depression, sedation, constipation, physical dependence and development of tolerance [26, 27], opioid agonists have long been the mainstay analgesics for the treatment of various pain states because of their potency, efficacy and availability. Three classical opioid receptors, namely μ-, δ- and κ-opioid receptors (MOR, DOR and KOR, respectively), have been identified in the central nervous system by pharmacological studies 28, 29], The common opioid drugs including morphine, codeine, oxycodone, methadone, heroin, morphine-6β-glucuronide (M6G), fentanyl, etc., which are used clinically for analgesic effects, mainly targets the MOR. Most studies have confirmed that the μ-opioid receptor is primarily responsible for the antinociceptive activity. However, a number of studies have suggested that ligands with dual μ- and δ-agonist activities display better biological profiles compared to the ones acting selectively on MOR [30, 31], There is also evidence that the presence of DOR agonists can improve the analgesic efficacy of MOR agonists [32, 33], KORs, broadly found in the spinal cord, the dorsal ganglia, the periphery and the supraspinal regions, are associated with pain modulation.

To overcome the difficulties in pain treatment described above, new approaches to drug design are needed to deal with recent observations that in the development of prolonged and neuropathic pain states, there are critically important changes in the expressed genome in ascending and descending pain pathways, and in the CNS that result from up regulation of neurotransmitter receptors and their ligands that are stimulatory and thus can cause pain. These anti-opioid ligands and receptors need to be considered in drug design. Therefore, there is a need to develop approaches to design ligands that are multivalent and therefore can act at two, three or more receptors all with a single molecule. The present invention provides such new approaches.

Here, it should be mentioned that the in-depth molecular-level understanding of the interactions between opioid ligands and their receptors is also very important for successful design of new drugs. Recent reports on how opioid ligands bind to their receptors by high-resolution crystal structures of three opioid receptor subtypes, i.e., the MOR [34], DOR [35], and KOR [36] have opened an additional opportunity to discover novel ligands targeting these G-Protein Coupled Receptors (GPCRs) that might ultimately be developed into more useful therapeutics [37, 38], However, it is important to note that the X-ray structures (conformations) of opioid receptors were occupied by antagonists and the conformation of agonist occupied receptors will clearly be different from an antagonist occupied receptor. Agonists and antagonists clearly have different SARs for opioid receptors.

The main clinically used drugs for the treatment of pain are opioid agonists. Although most of the currently used opioid drugs can act upon all three subtypes of opioid receptors, the drugs' analgesic effects are mainly due to the activation of MOR present in the central nervous system (CNS). One of the key reasons of having limited a number of centrally acting drugs is due to the presence of the blood-brain barrier (BBB), which put forward some constraint for foreign molecules to enter into the brain. The BBB permits hydrophobic and selected molecules to pass through it. But hydrophobic agents are difficult to transport via blood which requires more hydrophilic nature of the drug candidates. These two opposite requirements by the blood and the BBB have made it a challenging job for scientists to discover and develop new drugs, which can be delivered into the CNS. Another very important issue associated with development of centrally acting opioid drugs is their metabolic stability. This is because of the fact that therapeutic agents should have half-lives in the acceptable range so that they can interact with their biological targets for a sufficient duration of time to produce the desired response.

Investigational Opioid Receptor Agonists

To overcome the limitations of the currently used opioid drugs, many approaches have been taken over the last few decades ([39]). Literature in this field suggest that the issues of metabolic stability and blood-brain permeability should be taken into consideration at the very beginning stage of drug design. A drug candidate must be stable enough to the enzymatic action in the physiological systems so that it can reach the CNS. It should also cross the BBB to activate the receptors in the brain. Overcoming these two issues are highly challenging.

In published research work, C-terminal was modified by esterification and amidation. During the present study, amidation path has been given more importance over esterification because of the fact that amide linkage has shown better metabolic stability compared to the corresponding ester linkage. FIG. 1 illustrates the general path for synthesis of ligands in accordance with the present invention.

In spite of being highly potent shown during in vitro studies, many ligands fail to show their expected anti-nociceptive activity in animal models because of their poor bioavailability. These drugs can act most effectively if they interact with corresponding receptors in central nervous system, which is possible only when they cross the blood-brain barrier (BBB). As higher lipophilicity enhances a molecule's BBB permeability, our structural modifications could increase bioavailability leading to effective analgesic. We calculated the ALOGPs with the help of vcclab.org/lab/alogps/start.html and recorded the RP-HPLC retention times. Higher the ALOGPs or HPLC retention time higher is the lipophilicity.

Multivalent/multifunctional ligands were synthesized as described in FIG. 1 and FIG. 2 and Chaterjee et al, Nature Protocol, 2012, 7, 432-449. Binding affinities of these ligands were measured on radioligand binding assays[40]. Our well-established methods like isolated tissue-based functional assays using guinea pig ileum (GPI) and mouse isolated vas deferens (MVD) were employed for evaluating functional activities of the ligands 2-10[41, 42], Metabolic stability of selected ligands was examined by incubating the ligands in rat plasma at 37° C. ([43]).

Synthesis and characterization of ligands: All linear peptides were synthesized on solid phase using 2-chlorotrityl chloride resin (loading: 1.02 mmol/g) via Fmoc/$^t$Bu approach. All steps during solid phase synthesis were performed in frited syringes. N-methylation on desired amino acid was performed on solid phase following the procedure outlined in FIG. 2. C-terminal amidation was conducted in solution phase.

Loading of the first amino acid on the resin: Chlorotrityl resin (0.102 mmol) was swelled in dry dichloromethane (DCM) for 1 hour at room temperature. After swelling, dry DCM was expelled from the syringe and the resin was washed with DCM (1 mL, 3×1 min). It was then ready for the first amino acid coupling. Pre-generated (by treating with 5.0 equiv. DIPEA) carboxylate of Fmoc-Trp(Boc)-OH (1.2 equiv.) in dry DCM (1.0 mL) was loaded onto the resin by substituting chloride from the resin. After the coupling of first amino acid, methanol (0.1 mL) was added to the mixture and was shaken for 15 minutes in order to cap any unreacted chloride present in the resin. It was then washed with DCM (1 mL, 5×1 min) and DMF (1 mL, 4×1 min).

Deprotection: Following the washes, deprotection of Fmoc group was performed. This was done by stirring the resin with 20% piperidine in DMF for 8 minutes, followed by 12 minutes. A DMF wash (1 mL, 1 min) was performed in between the two deprotection steps to remove side products. After the second piperidine treatment, resin washes were performed with DMF (1 mL, 3×1 min), DCM (1 mL, 3×1 min), and DMF (1 mL, 3×1 min) before the next coupling. These steps were repeated after coupling of each Fmoc protected amino acid in the peptide sequence.

Coupling: For the coupling of the remaining amino acids, HCTU (3.0 equiv. and in case of primary amine) or HATU/HOAt (3.0 equiv. of each, in case of secondary amine) was used as coupling reagents and DIPEA (6.0 equiv.) as base. All couplings involving primary amines were carried out in DMF while coupling of secondary amine was performed in NMP. Between each coupling, resin washes were performed with DMF (1 mL, 3×1 min), DCM (1 mL, 3×1 min), and DMF (1 mL, 3×1 min).

After each coupling or deprotection, the Kaiser/chloranil test was performed to determine whether or not amino acid coupling or Fmoc deprotection was successful. Kaiser tests were run for primary amino acids and chloranil tests for secondary amino acids (e.g. proline and methylated amino acids). A negative test after each coupling suggests that the reaction was complete. After deprotection, the same test should be positive.

N-Methylation of amino acids: After Fmoc deprotection of the desired amino acid that will be N-methylated, o-NBS protection, N-methylation, and then o-NBS deprotection were performed.

o-NBS protection: After Fmoc deprotection, the resin was washed with DMF, DCM, then NMP (3×1 min each). NMP was drained out from the syringe. NMP (1 mL) was added to the resin followed by the addition of o-NBS-Cl (4 equiv.) and sym-collidine (10.0 equiv.). It was stirred for 15 minutes. The same step was repeated for one more time after filtering and washing the resin with NMP (1 mL, 1×1 min) in between. It was then washed with NMP (1 mL, 5×1 min) and then used for N-methylation.

N-methylation (DBU mediated method): DBU (1,8-diazabicyclo(5,4,0)undec-7-ene) (3.0 equiv.) in NMP (1 mL) was treated with the resin for 3 minutes. Afterwards and without filtering, DMS (10.0 equiv.) was added directly to the syringe containing resin and DBU solution and stir for another 3 min. The resin was then filtered and washed with NMP (1×1 min). This step was repeated once followed by filtration, and washing with NMP (5×1 min). The resultant resin bound peptide with N-methylation on amino acid was used for o-NBS deprotection.

o-NBS deprotection: NMP (1 mL), 2-mercaptoethanol (10.0 equiv.), and DBU (5.0 equiv.) were added to the syringe and the resin was treated for 5 min. The resin was filtered and washed with NMP (1 mL, 1×1 min). The procedure was repeated one more time and then the resin was filtered and washed with NMP (5×1 min).

General Procedure for Carbon-Carbon Double Bond Formation

After completing the linear sequence of the peptide, the resin-bound peptide was dried under vacuum, transferred to a 3-neck round bottom flask and suspended in approximately dry dichloromethane (10 mL/0.1 mmol of resin bound peptide). The mixture was kept under an argon atmosphere, and argon gas was bubbled into the reaction mixture for 30 minutes. Grubbs Catalyst 2nd Generation i.e. Dichloro[1,3-Bis(2,4,6-trimethylphenyl)-2-imidazolidinylidene](3-methyl-2-butenylidene)(tricyclohexylphosphine)ruthenium (II) (20 mol % with respect to the resin-bound peptide) was added to the reaction mixture and argon was again bubbled through the solution for an additional 30 minutes. The reaction mixture was then refluxed for 48 h. DMSO (50 equivalents with respect to the catalyst) was then added to the reaction mixture after allowing it to cool to room temperature. The reaction mixture was then stirred for an additional 24 hours. The resin-bound peptide was filtered and washed with DMSO, dichloromethane, and MeOH (3×5). The resin-bound peptide was dried under vacuum and used for next step. This method was used for making cabocycle-, lactone-, carbamate-based cyclic ligands.

Cleaving peptide from the resin: DIPEA (0.200 mL) was added to a centrifuge tube to trap excess TFA while collecting the peptide. The resin was stirred on a shaker with 1% TFA (2 mF/0.102 mmol of starting resin) in DCM (3×5 min) on the shaker. The resin was rinsed in between cleavage with small amounts of DCM. The peptide containing solution was collected in the centrifuge tube. Resin became darker with each TFA treatment. Volatiles were evaporated from the centrifuge tube by flushing the resulting solution with argon.

Amidation: The crude peptide was dissolved in dry DMF (1 mL) followed by addition of HATU (1.0 equiv.), HOAt (1.0 equiv.), DIPEA (4.0 equiv), and 3,5-bis(trifluoromethyl) benzylamine (1.1 equiv.), respectively and mixture was stirred for overnight. Workup: $KHSO_4$ (0.5 M in $H_2O$, 5 mL) was added to reaction mixture followed by extraction with DCM (3×15 mL). The combined organic extract was taken into a separatory funnel and was washed with brine (1×15 mL). The organic part was washed with $NaHCO_3$ (1×15 mL) followed by another brine wash. The final organic solution was dried over anhydrous sodium sulfate; gravity filtrated, and then evaporated under pressure to remove DCM in a round bottom flask (RBF).

Removal of Boc/$^t$Bu protecting groups: The crude peptide was treated for 1 h with a cleavage cocktail containing 82.5% TFA, 5% $H_2O$, thioanisol, 5% phenol, and 2.5% 1,2-ethanedithiol to remove Boc/$^t$Bu protecting groups. After 1 h, the solution was flushed with argon to evaporate volatiles.

Precipitation: Hexanes wash (3×15 mL) was performed to remove low polar materials by vortexing the mixture with hexanes followed by centrifugation at 3300 rpm (3×5 min), each time replacing the hexanes layer. Washes with hexanes and dimethyl ether mixture (30:70, 3×15 mL) gave white precipitate in 80-100% as crude yield. Purification of crudes using RP-HPLC furnished the pure ligands in 20-40% overall yield for lilear peptides and 10-20% overall yield for cyclic peptides.

Methods for In Vitro Study hNK1/CHO Cell Membrane Preparation and Radioligand Binding Assay: Recombinant hNK1/CHO cells were grown to confluency in 37° C. 95% air and 5% $CO_2$, humidified atmosphere, in a Forma Scientific (Thermo Forma, Ohio) incubator in Ham's F12 medium supplemented with 10% fetal bovine serum, 100 U/mL penicillin, 100 μg/mL streptomycin, and 500 μg/mL geneticin. The confluent cell monolayers were then washed with $Ca^{2+}$, $Mg^{2+}$-deficient phosphate-buffered saline (PD buffer) and harvested in the same buffer containing 0.02% EDTA. After centrifugation at 2700 rpm for 12 min, the cells were homogenized in ice-cold 10 mM Tris-HCl and 1 mM EDTA, pH 7.4, buffer. A crude membrane fraction was collected by centrifugation at 18000 rpm for 12 min at 4° C., the pellet was suspended in 50 mM Tris-Mg buffer, and the protein concentration of the membrane preparation was determined by using Bradford assay. Bradford assay: Six different concentrations of the test compound were each incubated, in duplicates, with 20 μg of membrane homogenate, and 0.5 nM [$^3$H] SP (135 Ci/mmol, Perkin-Elmer, United States) in 1 mL final volume of assay buffer (50 mM Tris, pH 7.4, containing 5 mM $MgCl_2$, 50 μg/mL bacitracin, 30 μM bestatin, 10 μM captopril, and 100 μM phenylmethylsulfonylfluoride) SP at 10 μM was used to define the nonspecific binding. The samples were incubated in a shaking water bath at 25° C. for 20 min. The reaction was terminated by rapid filtration through Whatman grade GF/B filter paper (Gaithersburg, Md.) presoaked in 1% polyethyleneimine, washed four times each with 2 mL of cold saline, and the filter bound radioactivity was determined by liquid scintillation counting (Beckman LS5000 TD).

Data Analysis: Analysis of data collected from three independent experiments performed in duplicates is done using GraphPad Prizm 4 software (GraphPad, San Diego, Calif.). Log $IC_{50}$ values for each test compound were determined from nonlinear regression. The inhibition constant (Ki) was calculated from the antilogarithmic $IC_{50}$ value by the Cheng and Prusoff equation.

Guinea Pig Isolated Ileum/Longitudinal Muscle with Myenteric Plexus (GPI/LMMP): Male Hartley guinea pigs under $CO_2$ anesthesia were sacrificed by decapitation and a non-terminal portion of the ileum removed. The longitudinal muscle with myenteric plexus (LMMP) was carefully separated from the circular muscle and cut into strips as described previously (Porreca and Burks, 1983). These tissues were tied to gold chains with suture silk and mounted between platinum wire electrodes in 20 mL organ baths at a tension of 1 g and bathed in oxygenated (95:5 $O_2$:$CO_2$) Kreb's bicarbonate buffer at 37° C. They were stimulated electrically (0.1 Hz, 0.4 msec duration) at supramaximal voltage. Following an equilibration period, compounds were added cumulatively to the bath in volumes of 14-60:1 until maximum inhibition was reached. A dose-response curve of PL-017 was constructed to determine tissue integrity before analog testing.

Mouse Isolated Vas Deferens Preparation: Male ICR mice under $CO_2$ anesthesia were sacrificed by cervical dislocation and the vasa differentia removed. Tissues were tied to gold chains with suture silk and mounted between platinum wire electrodes in 20 mL organ baths at a tension of 0.5 g and bathed in oxygenated ($O_2$:$CO_2$=95:5) magnesium free Kreb's buffer at 37° C. They were stimulated electrically (0.1 Hz, single pulses, 2.0 msec duration) at supramaximal voltage as previously described[44]. Following an equilibration period, compounds were added to the bath cumulatively in volumes of 14-60:1 until maximum inhibition was reached. A dose-response curve of DPDPE was constructed to determine tissue integrity before analog testing.

Agonist and Antagonist Testing: Compounds were tested as agonists by adding cumulatively to the bath until a full dose-response curve was constructed or to a concentration of 1 M. Compounds were tested as antagonists by adding to the bath 2 minutes before beginning the cumulative agonist dose-response curves of the delta (DPDPE) or mu (PL-017) opioid agonists.

Analysis: Percentage inhibition was calculated using the average tissue contraction height for 1 min preceding the addition of the agonist divided by the contraction height 3 min after exposure to the dose of agonist. $IC_{50}$ values represent the mean of not less than 4 tissues. $IC_{50}$ and $E_{max}$ estimates were determined by computerized nonlinear least-squares analysis (FlashCalc).

In vitro metabolic stability: A stock solution (50 mg/mL in DMSO) of each compound in study was made. It was diluted 1000-fold into rat plasma (Pel-Freez Biologicals, Rogers, Ak.) resulting in an incubation concentration of 50 µg/mL. Incubation temperature was 37° C. 200 µL of aliquots were pipetted out at different time points (i.e. 1 min, 10 min, 30 min, 1 h, 2 h, 4 h, 6 h, 8 h, and 24 h). 300 µL of acetonitrile was added to it and vortexed followed by centrifugation at 15000 rpm for 15 min. The supernatant was taken and analyzed for the remaining amount of parent compound using RP-HPLC (Vydac 218TP C18 10µ, Length: 250 mm, ID: 4.6 mm). Each sample was run twice and each time in duplet.

In Vivo Study

Methods

Animals: Adult male Sprague-Dawley rats (225-300 g; Harlan, Indianapolis, Ind.) and ICR mice (15-20 g; Harlan, Indianapolis, Ind.) were kept in a temperature-controlled environment with lights on 07:00-19:00 with food and water available ad libitum. All animal procedures were performed in accordance with the policies and recommendations of the International Association for the Study of Pain, the National Institutes of Health, and with approval from the Animal Care and Use Committee of the University of Arizona for the handling and use of laboratory animals.

Surgical methods: Rats were anesthetized (ketamine/xylazine anesthesia, 80/12 mg/kg i.p.; Sigma-Aldrich) and placed in a stereotaxic head holder. The cistema magna was exposed and incised, and an 8-cm catheter (PE-10; Stoelting) was implanted as previously reported, terminating in the lumbar region of the spinal cord (Yaksh and Rudy, 1976). Catheters were sutured (3-0 silk suture) into the deep muscle and externalized at the back of the neck. After a recovery period (≥7 days) after implantation of the indwelling cannula, vehicle (10% DMSO: 90% $MPH_2O$) or AKG115 (0.1 µg; n=6/treatment) were injected in a 5 µL volume followed by a 9 µl saline flush. Catheter placement was verified at completion of experiments.

Behavioral Assay: Paw-flick latency [Hargreaves et al., 1988] was collected as follows. Rats were allowed to acclimate to the testing room for 30 minutes prior to testing. Basal paw withdrawal latencies (PWLs) to an infrared radiant heat source were measured (intensity=40) and ranged between 16.0 and 20.0 seconds. A cutoff time of 33.0 seconds was used to prevent tissue damage. After a single, intrathecal injection (i.t.) of AKG115 or vehicle, PWLs were re-assessed up to 8 times post-injection.

In follow-up studies with AKG127, we chose a mouse model of acute thermal pain (Tail flick latency—TFL) and administered our compound by lumbar puncture (Hylden and Wilcox, 1980) to eliminate the need for intrathecal catheters. Briefly, the latency to tail withdrawal (TFL) from a 52° C. water bath were measured before (baseline) intrathecal injection of AKG127 (0.1 µg in 5 µL volume, n=6-8/treatment). Tail flick latencies were re-assessed at up to 8 time points after administration. At cut-off latency of 10.0 s was implemented to prevent tissue damage to the distal third of the tail. Mice with baseline TFLs<3 s or >9 s were excluded from the study.

For both studies, maximal percent efficacy was calculated and expressed as:

% Antinociception=100*(test latency after drug treatment−baseline latency)/(cutoff−baseline latency)

Statistics: Between group data were analyzed by non-parametric two-way analysis of variance (ANOVA; post hoc. Neuman-Kuels) in FlashCalc (Dr. Michael H. Ossipov, University of Arizona, Tucson, Ariz., USA). Within group data were analyzed by non-parametric one-way analysis of variance (ANOVA; post hoc: Bonferroni) in FlashCalc (Dr. Michael H. Ossipov, University of Arizona, Tucson, Ariz., USA). Differences were considered to be significant if P≤0.05. All data were plotted in GraphPad Prism 6. Compounds: AKG115 and AKG127 were prepared in 10% DMSO in 90% $MPH_2O$ Result and Discussion In vitro biological study: During our investigation, we tried to find the multivalent/multifunctional ligands with different ratios of binding affinities and agonist activity at MOR and DOR while showing their high affinity and antagonist activity at NK1R. To achieve this, we introduced unnatural amino acids including Dmt (2,6-dimethyl tyrosine), D-alanine, TV-methylated amino acids, 4-Abz, 4-Amb, 4-Apac, 4-Ampa, and chiral benzyl amine etc. in the ligands.

In some embodiments, opioid and NK-1 pharmacophores were directly connected with each other without any linker. The main changes made during this study are the introduction of unnatural amino acids (e.g., Tyr and Phe derivatives), and TV-methylated amino acids.

TABLE I

Physicochemical properties of the ligands

| Ligand ID | Molecular Formula | ALOGPs | HPLC RT (min) | ESI (M + H)+ Obsd. | ESI (M + H)+ Calcd. |
|---|---|---|---|---|---|
| TY012 | $C_{54}H_{61}F_6N_9O_8$ | 5.32 | 26.1 | HRMS | 1077.4547 |
| AKG117 | $C_{55}H_{63}F_6N_9O_8$ | 5.56 | 26.0 | 1092.4782 | 1092.4782 |
| AKG115 | $C_{57}H_{67}F_6N_9O_8$ | 5.80 | 26.6 | 1120.5091 | 1120.5095 |
| AKG116 | $C_{66}H_{81}F_6N_9O_{12}$ | 5.60 | 26.7 | 1106.4937 | 1106.4939 |
| AKG127 | $C_{56}H_{64}F_7N_9O_8$ | 4.42 | 26.8 | 1124.4844 | 1124.4844 |
| AKG128 | $C_{57}H_{66}F_7N_9O_8$ | 5.82 | 26.6 | 1138.4995 | 1138.5001 |
| AKG190 | $C_{54}H_{60}F_7N_9O_8$ | 5.24 | 26.1 | 1096.4530 | 1096.4531 |
| AKG191 | $C_{56}H_{64}ClF_6N_9O_8$ | 5.75 | 28.2 | 1140.4543 | 1139.4471 |
| AKG192 | $C_{56}H_{64}BrF_6N_9O_8$ | 5.52 | 28.4 | 1184.4040, 1186.4032 | 1184.4044, 1186.4023 |
| AKG193 | $C_{56}H_{64}F_6IN_9O_8$ | 5.73 | 28.5 | 1232.3894 | 1232.3905 |
| AKG180 | $C_{57}H_{67}F_6N_9O_8$ | 5.76 | 26.9 | 1120.3 | 1120.5095 |
| AKG181 | $C_{57}H_{67}F_6N_9O_8$ | 5.85 | 27.0 | 1120.3 | 1120.5095 |
| AKG182 | $C_{58}H_{69}F_6N_9O_8$ | 5.86 | 28.8 | 1134.1 | 1134.5252 |
| AKG183 | $C_{58}H_{69}F_6N_9O_8$ | 5.87 | 27.5 | 1134.3 | 1134.5252 |
| AKG184 | $C_{58}H_{69}F_6N_9O_8$ | 5.86 | 26.5 | 1134.3 | 1134.5252 |
| AKG185 | $C_{59}H_{71}F_6N_9O_8$ | 5.90 | 26.9 | 1148.2 | 1148.5408 |

AKG117: H-Tyr-D-Ala-Gly-NMePhe-Pro-Leu-Trp-NH-Bn(3',5'-(CF3)2) (SEQ ID NO: 11);
AKG115: H-Dmt-D-Ala-Gly-NMePhe-Pro-Leu-Trp-NH-Bn(3',5'-(CF3)2) (SEQ ID NO: 12);
AKG116: H-Dmt-D-Ala-Gly-Phe-Pro-Leu-Trp-NH-Bn(3',5'-(CF3)2) (SEQ ID NO: 13);
AKG127: H-Dmt-D-Ala-Gly-Phe(4-F)-Pro-Leu-Trp-NH-Bn(3',5'-(CF3)2) (SEQ ID NO: 14);
AKG128: H-Dmt-D-Ala-Gly-NMePhe(4-F)-Pro-Leu-Trp-NH-Bn(3',5'-(CF3)2) (SEQ ID NO: 15);
AKG190: H-Tyr-D-Ala-Gly-Phe(4-F)-Pro-Leu-Trp-NH-Bn(3',5'-(CF3)2) (SEQ ID NO: 52);
AKG191: H-Dmt-D-Ala-Gly-Phe(4-Cl)-Pro-Leu-Trp-NH-Bn(3',5'-(CF3)2) (SEQ ID NO: 16);
AKG192: H-Dmt-D-Ala-Gly-Phe(4-Br)-Pro-Leu-Trp-NH-Bn(3',5'-(CF3)2) (SEQ ID NO: 17);
AKG193: H-Dmt-D-Ala-Gly-Phe(4-I)-Pro-Leu-Trp-NH-Bn(3',5'-(CF3)2) (SEQ ID NO: 18);
AKG180: H-Dmt-D-Ala-NMeGly-Phe-Pro-Leu-Trp-NH-Bn(3',5'-(CF3)2) (SEQ ID NO: 53);
AKG181: H-Dmt-D-NMeAla-Gly-Phe-Pro-Leu-Trp-NH-Bn(3',5'-(CF3)2) (SEQ ID NO: 54);
AKG182: H-Dmt-D-Ala-NMeGly-NMePhe-Pro-Leu-Trp-NH-Bn(3',5'-(CF3)2) (SEQ ID NO: 55);
AKG183: H-Dmt-D-NMeAla-NMeGly-Phe-Pro-Leu-Trp-NH-Bn(3',5'-(CF3)2) (SEQ ID NO: 56);
AKG184: H-Dmt-D-NMeAla-Gly-NMePhe-Pro-Leu-Trp-NH-Bn(3',5'-(CF3)2) (SEQ ID NO: 57);
AKG185: H-Dmt-D-NMeAla-NMeGly-NMePhe-Pro-Leu-Trp-NH-Bn(3',5'-(CF3)2) (SEQ ID NO: 58).

Previous research from our group showed that when the linker between opioid and NK1 pharmacophores are removed from the ligand TY027, the resulting ligand TY012 (where Met[5] is) became μ-selective. Ligand AKG117 is produced by replacement of Phe at 4th position of ligand TY012 by NMePhe. It showed 9 times binding selectivity for MOR over DOR receptors ($K_i^{\mu}$=27 nM, $K_i^{\delta}$=240 nM, Table II) while showing potent binding affinity at NK1 receptors ($K_i^{hNK1}$=3.4 nM, $K_i^{rNK1}$=61 nM, Table II) meaning no appreciable change in binding affinities while comparing those for TY012 ($K_i^{\mu}$=9.5 nM, $K_i^{\delta}$=72 nM, $K_i^{hNK1}$=0.61 nM, $K_i^{rNK1}$=33 nM, Table II). Functional assays with ligand AKG117 also showed no appreciable change in agonist activities at opioid receptors ($IC_{50}^{\mu}$=230 nM, $IC_{50}^{\delta}$=100 nM, Table III) compared to those for TY012 ($IC_{50}^{\mu}$=350 nM, $IC_{50}^{\delta}$=45 nM, Table III). So, introduction of NMePhe alone at 4th position has minimum impact in altering the in vitro biological profiles. Dmt is well known to increase the binding affinities at opioid receptors. The ligand AKG115, where Tyr at 1st position of ligand AKG117 was replaced by Dmt, showed 5 times binding selectivity for MOR ($K_i^{\mu}$=1 nM, $K_i^{\delta}$=5 nM, Table IV) and slightly more agonist activity at MOR over DOR ($IC_{50}^{\mu}$=21 nM, $IC_{50}^{\delta}$=31 nM, Table V) while showing its high binding affinity and antagonist activity at NK1 receptor ($K_i^{hNK1}$=2 nM, $K_i^{rNK1}$=48.3 nM, Table II; $K_e^{NK1}$=9.7 nM, Table III). This indicates that presence of Dmt at 1st position played a role in increasing binding affinities and agonist activities at μ/δ opioid receptors. To cross-check whether N-methylated Phe at 4th position in AKG115 had any impact in binding affinities and functional activities, ligand AKG116 having Phe in place of NMePhe was designed and synthesized keeping Dmt at 1st position. This ligand showed high but balanced binding affinities for both μ and δ opioid receptors ($K_i^{\mu}$=3 nM, $K_i^{\delta}$=1 nM, Table II). But, its functional assays showed 26 times less agonist activity at MOR compared to that at DOR ($IC_{50}^{\mu}$=80.8 nM, $IC_{50}^{\delta}$=3.1 nM, Table III). It produced slightly increased binding affinity but small decrease in antagonist activity at NK1R ($K_i^{hNK1}$=1.4 nM, $K_i^{rNK1}$=27 nM, Table II; $K_e^{NK1}$=25 nM, Table III). From the results observed for ligands AKG117, AKG115 and AKG116 it is evident that presence of Dmt at 1st position and N-methylated Phe at 4th position is required for higher agonist activity at MOR than that at DOR. These results also are consistent with our previous observations that structural change at opioid pharmacophores can have impact in the biological profiles at NK1 receptors. Presence of halogens in drug candidates, especially in aromatic moieties, is known to play influential roles in their affinity and activities at biological targets. In ligands AKG127, AKG128, AKG190, AKG191, AKG192 and AKG193, we examined the effects of the presence of halogens. Though among halogen containing natural products, the presence of fluorine is less common, it has been found that presence of single or multiple fluorine atoms in synthetic drug candidates has profound effect in their biological profiles. In ligands AKG127, AKG128, and AKG190, we studied the effect of Phe(4-F) at 4th position with carrying some local structural changes in the opioid pharmacophore. When we replaced the Phe from ligand AKG116 by 4-fluorophenylalanine i.e. Phe(4-F) to produce ligand AKG127, it showed balanced binding affinities at MOR and DOR ($K_i^{\mu}$=1 nM, $K_i^{\delta}$=1 nM, Table II) while showing high affinity for NK1 receptors ($K_i^{hNK1}$=1 nM, $K_i^{rNK1}$=29 nM, Table III). But, the functional assay results showed 21 times selectivity for DOR over MOR while exerting high antagonist activity at NK1 receptor ($IC_{50}^{\mu}$=42 nM, $IC_{50}^{\delta}$=1.9 nM, $K_e^{NK1}$=5.3 nM, Table III). This might be due to the fact that all bonded ligands to MOR are not involved in its activation. To check the effect of combination of N-methylation and presence of fluorine, we synthesized the ligand AKG128, which contains N-methylated 4-fluorophenylalanine (NMe-Phe(4-F)) as its $4^{th}$ residue. It showed good binding affinity at all three receptors but with small selectivity for MOR over DOR ($K_i^\mu$=1 nM, $K_i^\delta$=4 nM, $K_i^{hNK1}$=2.6 nM, $K_i^{rNK1}$=34 nM, Table II). But, functional assays showed nearly 7 times lower agonist activity at MOR than that at DOR while maintaining antagonist activity at NK1R ($IC_{50}^\mu$=76.5 nM, $IC_{50}^\delta$=11 nM, $K_e^{NK1}$=11 nM, Table III). Substitution of Dmt at $1^{st}$ position by Tyr from ligand AKG127 gave ligand AKG190, which displayed selectivity for DOR over MOR in binding (20 times, $K_i^\mu$=4 nM, $K_i^\delta$=0.2 nM, Table II) as well as in functional assays (5 times, $IC_{50}^\mu$=65 nM, $IC_{50}^\delta$=12 nM, Table III). Then to investigate the effect of other halogens we synthesized ligands AKG191 containing Phe(4-Cl), AKG192 containing Phe(4-Br), and AKG193 containing Phe(4-I) as $4^{th}$ residue. All of them showed reduced binding affinities (Table II) as well as functional activities (Table III) at opioid receptors compared to the parent ligand AKG127. But they displayed comparable binding affinities (Table II) as well as functional activities (Table III) at NK1 receptors. Iodine containing ligand AKG193 became much less active at the MOR though it showed good affinity at the same receptor. This again indicates binding of ligand to a receptor does not necessarily mean that it involves in functional activities. Then we wanted to see the effect of N-methylation at different residues as well as the impact of multiple N-methylations. We designed and synthesized many ligands including AKG180, AKG181, AKG182, AKG183, AKG184, and AKG185. Their partial in vitro results are given in Table II.

TABLE II

Binding affinity results of representative ligands at opioid and NK1 receptors

| Ligand No. | $K_i^\mu$ (nM) | Log[$IC_{50}\pm$] | $K_i^\delta$ (nM) | Log[$IC_{50}\pm$] | $K_i^\mu/K_i^\delta$ | $K_i^{hNK1}$ (nM) | $K_i^{rNK1}$ (nM) | $K_i^{hNK1}/K_i^{rNK1}$ |
|---|---|---|---|---|---|---|---|---|
| TY012 | 9.5 | −7.7 ± 0.21 | 72 | −6.8 ± 0.08 | 1/8 | 0.6 | 33 | 1/54 |
| AKG117 | 27 (n = 6) | −7.05 ± 0.04 | 237 (n = 6) | −6.35 ± 0.13 | 1/9 | 3.35 ± 0.74 (n = 6) | 61.1 ± 2.0 (n = 6) | 1/18 |
| AKG115 | 1 (n = 6) | −8.78 ± 0.05 | 5 (n = 6) | −7.92 ± 0.07 | 1/5 | 2.23 ± 0.07 (n = 6) | 48.3 ± 8.32 (n = 6) | 1/22 |
| AKG116 | 3 (n = 6) | −8.63 ± 0.04 | 1 (n = 6) | −8.66 ± 0.03 | 3/1 | 1.4 ± 0.09 (n = 6) | 26.9 ± 1.98 (n = 6) | 1/19 |
| AKG127 | 1 (n = 6) | −8.72 ± 0.08 | 1 (n = 6) | −7.18 ± 0.04 | 1/1 | 0.88 ± 0.07 (n = 6) | 29.4 ± 1.5 (n = 6) | 1/33 |
| AKG128 | 1 (n = 2) | −8.55 ± 0.18 | 4 (n = 6) | −8.19 ± 0.08 | 1/4 | 2.62 ± 0.51 (n = 6) | 33.8 ± 6.2 (n = 6) | 1/13 |
| AKG190 | 4 (n = 2) | −8.08 ± 0.10 | 0.2 (n = 2) | 7.65 ± 0.07 | 20/1 | 5.61 ± 0.65 (n = 6) | 34.4 ± 2.8 (n = 6) | 1/6 |
| AKG191 | 2 (n = 2) | −8.33 ± 0.09 | 5 (n = 6) | −8.02 ± 0.03 | 1/2.5 | 2.9 ± 0.53 (n = 6) | 26.5 ± 5.3 (n = 6) | 1/9 |
| AKG192 | 5 (n = 2) | −7.96 ± 0.12 | 16 (n = 4) | −7.71 ± 0.06 | 1/2 | 2.54 ± 0.21 (n = 6) | 47.4 ± 12.6 (n = 6) | 1/19 |
| AKG193 | 6 (n = 2) | −7.88 ± 0.07 | 10 (n = 4) | −7.53 ± 0.08 | 1/3 | 3.29 ± 0.6 (n = 6) | 38.8 ± 3.6 (n = 6) | 1/12 |
| AKG180 | N.D. | N.D. | N.D. | N.D. | —/— | 2.86 (n = 4) | 17.1 ± 2.9 (n = 6) | 1/6 |
| AKG181 | N.D. | N.D. | N.D. | N.D. | —/— | 4.81 ± 1.39 | 26.4 ± 9.3 (n = 6) | 1/5 |
| AKG182 | N.D. | N.D. | N.D. | N.D. | —/— | 5.00 (n = 4) | 110.0 ± 18.3 (n = 6) | 1/22 |
| AKG183 | N.D. | N.D. | N.D. | N.D. | —/— | 2.49 (n = 4) | 17.6 ± 10. (n = 6) | 1/7 |
| AKG184 | N.D. | N.D. | N.D. | N.D. | —/— | 2.84 (n = 4) | 114.8 (n = 4) | 1/40 |
| AKG185 | N.D. | N.D. | N.D. | N.D. | —/— | 3.47 (n = 4) | 74.83 (n = 4) | 1/21 |

N.D. means not determined,
n in the parenthesis indicates number of run

TABLE III

Functional assay results of representative ligands

| Compd. Number | GPI (MOR) $IC_{50}$ (nM) | MVD (DOR) $IC_{50}$ (nM) | GPI/MVD $IC_{50}$ ratio | GPI/LMMP (NK1R) Agonist | $K_e$ (nM) ± S.E.M. |
|---|---|---|---|---|---|
| AKG117 | 231.7 ± 52.9 | 102.5 ± 33.6 | 2.3/1 | None at 100 nM | 21.1 ± 9.2 |
| AKG115 | 20.6 ± 3.52 | 30.7 ± 7.5 | 1/1.5 | None at 30 nM | 9.7 ± 1.2 |
| AKG116 | 80.8 ± 18.1 | 3.1 ± 1.0 | 26/1 | None at 100 nM | 24.9 ± 3.6 |
| AKG127 | 41.6 ± 9.68 | 1.96 ± 0.680 | 21.2/1 | None at 30 nM | 5.3 ± 1.64 |
| AKG128 | 76.5 ± 14.96 | 11.5 ± 5.6 | 6.6/2 | None at 30 nM | 11.2 ± 2.7 |
| AKG190 | 64.8 ± 9.2 | 12.1 ± 4.0 | 5.3/1 | None at 30 nM | 5.8 ± 1.9 |
| AKG191 | 166.2 ± 71.6 | 25.4 ± 7.7 | 6.5/1 | None at 300 nM | 44.1 ± 7.7 |
| AKG192 | 463.4 ± 114.3 | 43.0 ± 11.6 | 10.8/1 | None at 100 nM | 23.4 ± 8.9 |
| AKG193 | 41% at 1 uM | 97.2 ± 20.5 | —/— | None at 300 nM | 41.9 ± 5.9 |

For every sample, the number of run was four at each receptor

In other embodiments, a wide variety of natural and unnatural amino acids that have been incorporated as a linker and/or an address region. For the first time, aromatic rigid linkers, e.g., 4-Amb, 4-Abz, 4-Apac, etc., have been introduced to reduce the interference of opioid and NK-1 pharmacophores in each other's activity. N-methylated unnatural amino acids also were used during this study.

TABLE IV

Physicochemical properties of the ligands

| Ligand ID | Molecular Formula | ALOGPs | HPLC RT (min) | ESI (M + H)+ Obsd. | ESI (M + H)+ Calcd. |
|---|---|---|---|---|---|
| TY045 | $C_{60}H_{72}F_6N_{10}O_9$ | 5.66 | 27.6 |  | 1190.5388 |
| AKG112 | $C_{61}H_{74}F_6N_{10}O_9$ | 5.85 | 27.7 | 1205.5623 | 1205.5623 |
| AKG113 | $C_{57}H_{66}F_6N_{10}O_9$ | 5.07 | 25.8 | 1149.4989 | 1149.4997 |
| AKG130 | $C_{56}H_{63}F_7N_{10}O_9$ | 4.71 | 25.4 | 1153.4739 | 1153.4746 |
| AKG131 | $C_{57}H_{65}F_7N_{10}O_9$ | 4.99 | 25.7 | 1167.4896 | 1167.4902 |
| AKG119 | $C_{58}H_{68}F_6N_{10}O_9$ | 5.17 | 25.6 | 1163.5149 | 1163.5153 |
| AKG123 | $C_{59}H_{70}F_6N_{10}O_9$ | 5.33 | 26.2 | 1177.5307 | 1177.5310 |
| AKG124 | $C_{61}H_{74}F_6N_{10}O_9$ | 5.61 | 26.4 | 1205.5626 | 1205.5623 |
| AKG125 | $C_{63}H_{70}F_6N_{10}O_9$ | 5.82 | 26.3 | 1225.5303 | 1225.5310 |
| AKG176 | $C_{62}H_{68}F_6N_{10}O_9$ | 5.62 | 26.9 | 1211.5148 | 1211.5153 |
| AKG177 | $C_{63}H_{70}F_6N_{10}O_9$ | 5.73 | 27.2 | 1225.5304 | 1225.5310 |
| AKG178 | $C_{64}H_{72}F_6N_{10}O_9$ | 5.90 | 27.1 | 1239.5462 | 1239.5466 |
| AKG179 | $C_{65}H_{74}F_6N_{10}O_9$ | 5.93 | 28.0 | 1253.5648 | 1253.5623 |
| AKG106 | $C_{60}H_{72}F_6N_{10}O_9S$ | 5.57 | 27.3 | 1223.5238 | 1223.5187 |
| AKG107 | $C_{62}H_{76}F_6N_{10}O_9S$ | 5.84 | 27.8 | 1251.5549 | 1251.5500 |

TY045: H-Tyr-D-Ala-Gly-Phe-Nle-Pro-Leu-Trp-NH-Bn(3',5'-(CF$_3$)$_2$) (SEQ ID NO:59);
AKG112: H-Tyr-D-Ala-Gly-NMePhe-Nle-Pro-Leu-Trp-NH-Bn(3',5'-(CF$_3$)$_2$) (SEQ ID NO:60);
AKG113: H-Tyr-D-Ala-Gly-NMePhe-Gly-Pro-Leu-Trp-NH-Bn(3',5'-(CF$_3$)$_2$) (SEQ ID NO:61);
AKG130: H-Tyr-D-Ala-Gly-Phe(4-F)-Gly-Pro-Leu-Trp-NH-Bn(3',5'-(CF$_3$)$_2$) (SEQ ID NO:62);
AKG131: (SEQ ID NO: 10, where Tyr'=Tyr, R on Ala is methyl, Phe' is NMePhe(4-F), x =1, AA is Gly, R on Leu, Trp is H, and XCH(R) Ph(R')$_2$ is NHCH$_2$(3,5-difluorophenyl);
AKG119: (SEQ ID NO: 19, where Tyr'=Tyr, R on Ala, Gly, Leu, and Trp is H, Phe'=NMePhe, x=1, AA = β-Ala, and XCH(R) Ph(R')$_2$ is NHCH$_2$(3,5-difluorophenyl);
AKG123: (same as AKG119 except AA=4-Abu);
AKG124: (same as AKG119 except AA=6-Ahx);
AKG125: (same as AKG119 except AA=4-Amb);
AKG176: (same as AKG119 except AA=4-Abz);
AKG177: (same as AKG119 except AA=4-Apac);
AKG178: (same as AKG119 except AA=4-Ampa);
AKG179: (same as AKG119 except Tyr' is Dmt and AA=4-Abu);
AKG106: (same as AKG119 except AA=Met);
AKG107: (same as AKG119 except Tyr' = Dmt and AA=Met).

This study was started taking ligand TY045, which showed selectivity for MOR over DOR, as a reference. As we have observed the biasedness for MOR because of the introduction of NMe-Phe at the 4$^{th}$ position, we replaced Phe by the same to get more selectivity for MOR. Ligand AKG112 containing NMe-Phe as 4$^{th}$ residue and Nle as 5$^{th}$ residue showed small binding selectivity (1.7 time) for MOR over DOR ($K_i^\mu$=13 nM, $K_i^\delta$=22 nM, Table V) while showing nanomolar range binding affinity at NK1R ($K_i^{hNK1}$=3.8 nM, $K_i^{rNK1}$=19 nM, Table V). However, functional activity studies showed that it has higher agonist activity at DOR compared to that at MOR ($IC_{50}^\mu$=718.5 nM, $IC_{50}^\delta$=12 nM, $K_e^{NK1}$=5.4 nM, Table V). In search of further increase of μ-selectivity substitution of Nle from AKG112 by relatively flexible Gly was made to produce ligand AKG113. This ligand exhibited 15 times binding selectivity ($K_i^\mu$=3 nM, $K_i^\delta$=46 nM, Table V) but with small reduction in binding affinity at rat NK1 ($K_i^{hNK1}$=2.1 nM, $K_i^{rNK1}$=60 nM, Table V). Functional assays showed that it has two times higher agonist activity at DOR compared to that at MOR while exhibiting high antagonist activity at NK1R ($IC_{50}^\mu$=79.20 nM, $IC_{50}^\delta$=39 nM, $K_e^{NK1}$=15 nM, Table V). To examine the effect of fluorine, we synthesized ligands AKG130 and AKG131, which were obtained due to the replacement of 4$^{th}$ residue of AKG113, i.e. Phe by Phe(4-F) and NMePhe(4-F), respectively. Both the ligands showed binding selectivity for DOR binding (AKG130: $K_i^\mu$=9 nM, $K_i^\delta$=5 nM; AKG131: $K_i^\mu$=185 nM, $K_i^\delta$=17 nM, Table V) with reduced binding affinity at rat NK1R (AKG130: $K_i^{hNK1}$=1.54 nM, $K_i^{rNK1}$=72 nM; AKG131: $K_i^{hNK1}$=2 nM, $K_i^{rNK}$1=89 nM, Table V). Both of these ligands displayed higher agonist activity at DOR compared to that at DOR NK1R (AKG130: $IC_{50}^\mu$=340 nM, $IC_{50}^\delta$=12 nM, $K_e^{NK1}$=11 nM; AKG131: $IC_{50}^\mu$=63 nM, $IC_{50}^\delta$=30 nM, $K_e^{NK1}$=36 nM; Table V). Next, to examine the impact of longer and flexible linker/address region, we designed and synthesized ligands AKG119, AKG123 and AKG124, which are the products because of the substitution of 5$^{th}$ residue of AKG113 i.e., Gly by β-Ala, γ-Abu and 6-Ahx, respectively. All these ligands showed binding affinities at nanomolar range. However, no significant increase in opioid receptor binding selectivity was found (Table V). Functional assays showed 7-10 times higher agonist activity at DOR compared to that at MOR (Table V). We noticed that modification of opioid pharmacophore was impacting binding affinities at opioid receptors as well as at NK1R. At this point we thought that introduction of a rigid linker in between opioid and NK1 receptors might reduce the interference of each receptor in other's biological profile. We replaced 5$^{th}$ residue Gly from AKG113 by relatively rigid linker 4-Amb to obtain ligand AKG125. This new ligand exhibited 23 times binding selectivity for MOR over DOR ($K_i^\mu$=5 nM, $K_i^\delta$=120 nM, Table V) while maintaining nanomolar affinity at NK1 receptors ($K_i^{hNK1}$=2.3 nM, $K_i^{rNK1}$=30 nM, Table V).). However, it produced 10 times higher agonist activity at DOR ($IC_{50}^{\mu}$=470 nM, $IC_{50}^{\delta}$=46 nM, $K_e^{NK1}$=8.4 nM, Table V). This result prompted us to design and synthesize ligands AKG176, AKG177 and AKG178 containing 4-Abz, 4-Apac and 4-Ampa as linkers, respectively. Ligand AKG176 having the most rigid linker showed higher affinity at MOR ($K_i^{\mu}$=1 nM, $K_i^{\delta}$=70 nM, Table V) while maintaining good NK1R binding affinity ($K_i^{hNK1}$=5.3 nM, $K_i^{rNK1}$=74 nM, Table V). Ligand AKG177 displayed almost equal agonist activity at MOR and DOR ($IC_{50}^{\mu}$=41 nM, $IC_{50}^{\delta}$=35 nM, Table V) while showing high antagonist activity at NK1R ($K_e^{NK1}$=39 nM, Table V). Ligand AKG178, which has an address region moiety of aromatic rigidity in the middle with two flexible arms at 180 degree angle, have shown high binding affinity DOR ($K_i^{\delta}$=100 nM, Table IV) as well as NK1 receptors ($K_i^{hNK1}$=3.5 nM, $K_i^{rNK1}$=72 nM, Table IV). But, it showed 15 times higher agonist activity at DOR in functional assays ($IC_{50}^{\mu}$=650 nM, $IC_{50}^{\delta}$=44 nM, $K_e^{NK1}$=76 nM, Table V). AKG179 was designed and synthesized by replacing the Tyr by Dmt position to increase the binding affinities and functional activities at opioid receptors. Its SAR study is in progress. In addition, ligands AKG106 and AKG107 were designed and synthesized by replacing $4^{th}$ residue i.e. Phe of TY027 (H-Tyr-D-Ala-Gly-Phe-Met-Pro-Leu-Trp-NH-Bn(3',5'-(CF$_3$)$_2$)) and TY032 (H-Dmt-D-Ala-Gly-Phe-Met-Pro-Leu-Trp-NH-Bn(3',5'-(CF$_3$)$_2$)) by NMePhe. These ligands have shown high binding affinities at NK1R (TY027: $K_i^{NK1}$=1.5 nM, $K_i^{rNK1}$=10 nM; TY027: $K_i^{NK1}$=2 nM, $K_i^{rNK1}$=14 nM; Table I).

TABLE V

Binding affinity results at opioid and NK1 receptors

| Ligand No. | $K_i^{\mu}$ (nM) | Log[$IC_{50}\pm$] | $K_i^{\delta}$ (nM) | Log[$IC_{50}\pm$] | $K_i^{\mu}/K_i^{\delta}$ | $K_i^{hNK1}$ (nM) | $K_i^{rNK1}$ (nM) | $K_i^{hNK1}/K_i^{rNK1}$ |
|---|---|---|---|---|---|---|---|---|
| AKG112 | 13 (n = 2) | −7.51 ± 0.04 | 22 (n = 2) | −7.30 ± 0.05 | 1/1.7 | 14.0 ± 3.1 (n = 6) | 19.12 ± 7.88 | 1/1.4 |
| AKG113 | 3 (n = 2) | −8.23 ± 0.03 | 46 (n = 2) | −7.00 ± 0.06 | 1/15 | 15.0 ± 4.06 (n = 6) | 60.5 ± 2.9 (n = 6) | 1/4 |
| AKG130 | 9 (n = 2) | −7.69 ± 0.06 | 5 (n = 2) | −7.96 ± 0.04 | 2/1 | 1.54 ± 0.12 (n = 6) | 72.5 ± 10.0 (n = 6) | 1/47 |
| AKG131 | 185 (n = 2) | −6.40 ± 0.32 | 17 (n = 2) | −7.42 ± 0.07 | 11/1 | 2.14 ± 0.31 (n = 6) | 89.1 ± 11.6 (n = 6) | 1/8 |
| AKG119 | 8 (n = 2) | −7.76 ± 0.11 | 46 (n = 2) | −6.97 ± 0.05 | 1/5.6 | 0.93 ± 0.14 (n = 6) | 29.43 ± 2.66 (n = 6) | 1/32 |
| AKG123 | 9 (n = 2) | −7.73 ± 0.07 | 3 (n = 2) | −8.23 ± 0.05 | 3/1 | 1.56 ± 0.27 (n = 6) | 57.0 ± 1.9 (n = 6) | 1/37 |
| AKG124 | 7 (n = 2) | −7.80 ± 0.09 | 31 (n = 2) | −7.14 ± 0.03 | 1/4.4 | 1.22 ± 0.3 (n = 6) | 44.3 ± 2.9 (n = 6) | 1/36 |
| AKG125 | 5 (n = 2) | −7.92 ± 0.11 | 117 (n = 2) | −6.58 ± 0.06 | 1/23.4 | 2.27 ± 0.68 (n = 6) | 29.9 ± 7.6 (n = 6) | 1/13 |
| AKG176 | 1 (n = 2) | −8.69 ± 0.24 | 82 (n = 6) | −6.74 ± 0.16 | 1/82 | 4.12 ± 0.94 (n = 6) | 77.8 ± 4.8 (n = 6) | 1/19 |
| AKG177 | 1 (n = 2) | −8.68 ± 0.19 | 70 (n = 4) | −6.83 ± 0.06 | 1/70 | 5.28 ± 1.15 (n = 6) | 74.3 ± 12.07 (n = 6) | 1/14 |
| AKG178 | N.D. | N.D. | 100 (n = 4) | −6.64 ± 0.17 | —/— | 3.50 ± 1.05 (n = 6) | 72.3 ± 11.2 (n = 6) | 1/21 |
| AKG106 | N.D. | N.D. | N.D. | N.D. | —/— | 1.47 ± 1.8 (n = 6) | 9.9 ± 2.3 (n = 6) | 1/7 |
| AKG107 | N.D. | N.D. | N.D. | N.D. | —/— | 1.97 ± 2.6 (n = 6) | 13.6 ± 1.4 (n = 6) | 1/7 |

N.D. means not determined,
n in the parenthesis indicates number of run

TABLE VI

Functional assay results

| Compd. Number | GPI (MOR) $IC_{50}$ (nM) | MVD (DOR) $IC_{50}$ (nM) | GPI/MVD $IC_{50}$ ratio | GPI/LMMP (NK1R) Agonist | $K_e$ (nM) ± S.E.M. |
|---|---|---|---|---|---|
| AKG112 | 718.5 ± 168.7 | 11.63 ± 2.55 | 62/1 | None at 30 nM | 5.4 ± 2.1 |
| AKG113 | 79.20 ± 5.52 | 38.74 ± 9.69 | 2/1 | None at 100 nM | 14.9 ± 2.9 |
| AKG130 | 339.4 ± 120.0 | 11.91 ± 1.56 | 28.5/1 | None at 300 nM | 10.6 ± 3.54 |
| AKG131 | 62.55 ± 19.29 | 29.71 ± 9.73 | 2/1 | None at 100 nM | 35.8 ± 10.8 |
| AKG119 | 365.4 ± 185.5 | 36.67 ± 4.18 | 10/1 | None at 100 nM | 20.8 ± 3.8 |
| AKG123 | 423.6 ± 147.8 | 50.08 ± 17.43 | 8.5/1 | None at 100 nM | 2.3 ± 0.7 |
| AKG124 | 254.7 ± 71.2 | 36.82 ± 13.59 | 7/1 | None at 100 nM | 11.2 ± 3.1 |
| AKG125 | 471.1 ± 273.2 | 46.26 ± 13.42 | 10/1 | None at 100 nM | 8.36 ± 4.12 |
| AKG176 | 40.79 ± 8.00 | 22.78 ± 5.53 | 2/1 | None at 300 nM | 116.6 ± 31.4 |
| AKG177 | 40.82 ± 6.00 | 35.01 ± 7.89 | 1/1 | None at 100 nM | 39.2 ± 7.9 |
| AKG178 | 654.0 ± 76.7 | 44.02 ± 16.00 | 15/1 | None at 300 nM | 76.4 ± 11.2 |

For every sample, the number of run was four at each receptor

In other embodiments, DAMGO (H-Tyr-D-Ala-Gly-NMePhe-Gly-ol) derived pharmacophores are incorporated in the opioid part of the new ligands. The side chain of the 5$^{th}$ residue contained functional groups like free alcoholic hydroxyl (—OH), and amine (—NH$_2$). N-methylated unnatural amino acids have been used during this study.

TABLE VII

Physicochemical properties of the ligands

| Ligand ID | Molecular Formula | ALOGPs | HPLC RT (min) | ESI (M + H)$^+$ Obsd. | ESI (M + H)$^+$ Calcd. |
|---|---|---|---|---|---|
| AKG038 | $C_{57}H_{66}F_6N_{10}O_{10}$ | 4.16 | 25.5 | 1165.3 | 1165.4946 |
| AKG039 | $C_{58}H_{68}F_6N_{10}O_{10}$ | 4.31 | 25.2 | 1179.3 | 1179.5102 |
| AKG101 | $C_{57}H_{66}F_6N_{10}O_{10}$ | 4.16 | 28.5 | 1165.3 | 1165.4946 |
| AKG126 | $C_{58}H_{68}F_6N_{10}O_{10}$ | 4.52 | 25.6 | 1179.5077 | 1179.5102 |
| AKG132 | $C_{60}H_{72}F_6N_{10}O_{10}$ | 4.71 | 26.1 | 1207.5397 | 1207.5415 |
| AKG133 | $C_{57}H_{65}F_7N_{10}O_{10}$ | 4.10 | 25.3 | 1183.4839 | 1183.4852 |
| AKG134 | $C_{58}H_{67}F_7N_{10}O_{10}$ | 4.39 | 25.4 | 1197.4989 | 1197.5008 |
| AKG135 | $C_{60}H_{71}F_7N_{10}O_{10}$ | 4.65 | 26.0 | 1225.5293 | 1225.5321 |
| AKG-CRA-136 | $C_{60}H_{71}F_6N_{11}O_{11}$ | 4.13 | 25.0 | 1236.5302 | 1236.5317 |
| AKG-CRA-137 | $C_{62}H_{75}F_6N_{11}O_{11}$ | 4.32 | 25.5 | 1264.5607 | 1264.5630 |
| AKG171 | $C_{58}H_{69}F_6N_{11}O_9$ | 4.20 | 24.0 | 1178.5247 | 1178.5262 |
| AKG172 | $C_{59}H_{71}F_6N_{11}O_9$ | 4.33 | 23.7 | 1192.5413 | 1192.5419 |
| AKG173 | $C_{60}H_{73}F_6N_{11}O_9$ | 4.48 | 23.8 | 1206.5568 | 1206.5575 |
| AKG174 | $C_{61}H_{75}F_6N_{11}O_9$ | 4.63 | 23.6 | 1220.5722 | 1220.5732 |

AKG038: (same as AKG119 except AA=Ser);
AKG039: (same as AKG119 except Phe'=Phe and AA=Homo-Ser); (same as AKG119 except Phe'=Phe, AA=D-Ser);
AKG126: (same as AKG119 except AA=Ser);
AKG132: (same as AKG119 except Tyr'=Dmt and AA=Ser);
AKG133: (same as AKG119 except Phe'=Phe(4-F) and AA=Ser);
AKG134: (same as AKG119 except Phe'=NMePhe(4-F) and AA=Ser);
AKG135: (same as AKG119 except Tyr'=Dmt, Phe'=NMePhe(4-F), and AA=Ser);
AKG-CRA-136: (same as AKG119 except x=2 and (AA)x = Ser Gly;
AKG-CRA-137: (same as AKG119 except Tyr'=Dmt, x=2 and (AA)x = Ser Gly;
AKG171: (same as AKG119 except AA=4-Dap);
AKG172: (same as AKG119 except AA=4-Dab);
AKG173: (same as AKG119 except AA=Orn);
AKG174: (same as AKG119 except AA=Lys).

We already have some ligands with higher agonist activities DOR compared to that at MOR. Here, we are trying to achieve higher binding as well as functional selectivity at MOR compared to those at DOR. We introduced the structural features of DAMGO (H-Tyr-D-Ala-Gly-NMe-Phe-Gly-ol), a MOR selective ligand in our opioid pharmacophore part. Ligand AKG038 was designed and synthesized by introducing serine (Ser) at the 5$^{th}$ position (Table VIII). It was expected to play the role similar to that played by glyol (Gly-ol) in DAMGO. This ligand showed 18 times higher binding affinity at DOR compared to that at MOR ($K_i^\mu$=130 nM, $K_i^\delta$=7 nM, Table VIII). This ligand showed low binding affinity at rNK1R ($K_i^{hNK1}$=2 nM, $K_i^{rNK1}$=210 nM, Table VIII). Functional assays showed 21 times higher agonist activity at DOR over DOR ($IC_{50}^\mu$=400 nM, $IC_{50}^\delta$=18 nM, $K_e^{NK1}$=5 nM, Table IX). We wanted to examine the effect of length of the side chain containing primary alcoholic group at 5$^{th}$ position. So, we replaced Ser by homo-serine (Homo-Ser) at 5$^{th}$ position and synthesized ligand AKG039. There was no significant change in binding affinities at opioid receptors as well as NK1R ($K_i^\mu$=120 nM, $K_i^\delta$=6 nM, $K_i^{hNK1}$=1.3 nM, $K_i^{rNK1}$=150 nM, Table VIII). It also displayed 21 times higher agonist activity at DOR ($IC_{50}^\mu$=130 nM, $IC_{50}^\delta$=6 nM, $K_e^{NK}$1=9.7 nM, Table IX). Though these two ligands showed nanomolar range binding affinities at human NK1R, poor binding affinities were observed at rat NK1R. Effect of chirality at 5$^{th}$ position was checked by introducing D-Ser in ligand AKG101 (Table VIII). It did not improve the binding affinities at MOR, DOR and NK1R ($K_i^\mu$=200 nM, $K_i^\delta$=34 nM, $K_i^{hNK1}$=3 nM, $K_i^{rNK1}$=110 nM, Table VIII). Functional assays showed that it had poor agonist activity at MOR ($IC_{50}^\mu$=39.7% at 1 µM, $IC_{50}^\delta$=6.7 nM, $K_e^{NK1}$=28 nM, Table IX). Replacement of Phe (of AKG038) by NMePhe produced ligand AKG126, which displayed 31 times binding selectivity for MOR over DOR while showing high affinity at NK1R ($K_i^\mu$=2 nM, $K_i^\delta$=63 nM, $K_i^{hNK1}$=1 nM, $K_i^{rNK1}$=31 nM, Table VIII). But, it displayed 9 times higher agonist activity at DOR over MOR ($IC_{50}^\mu$=240 nM, $IC_{50}^\delta$=26 nM, $K_e^{NK1}$=17 nM, Table IX). We have observed that the presence of Dmt at 1$^{st}$ position of opioid ligands significantly increases the binding affinity. Ligand AKG132 was designed and synthesized by introducing Dmt at 1$^{st}$ position. It showed the expected higher affinity at opioid receptors but with reduced binding selectivity ($K_i^\mu$=0.4 nM, $K_i^\delta$=2 nM, $K_i^{hNK1}$=5.6 nM, $K_i^{rNK1}$=36 nM, Table VIII). It also displayed delta selectivity over mu ($IC_{50}^\mu$=43 nM, $IC_{50}^\delta$=7.7 nM, $K_e^{NK1}$=20 nM, Table IX). Ligands AKG133, AKG134 and AKG135 were designed and synthesized using AKG038, AKG126 and AKG132 as references, respectively; we examined the effect of fluorine (F) in the para position of Phe (Table VII). All of them showed high binding affinities (nanomolar range) at all three receptors (Table VIII). However, they failed to produce appreciable binding selectivity. All these three ligands displayed higher agonist activity at DOR compared to that at MOR with strong antagonist activity at NK1R (Table IX). However, ligand AKG135 showed high and close agonist activity at both the opioid receptors studied ($IC_{50}^\mu$=23 nM, $IC_{50}{}^\delta$=15 nM, $K_e{}^{NK1}$=29 nM, Table VI). To examine the effect of the length of linker, we introduced Gly as $6^{th}$ residue in ligands AKG-CRA-136 and AKG-CRA-137 (Table VII). Ligand AKG-CRA-137 showed balanced binding affinities at MOR and DOR while showing good affinity at NK1R ($K_i{}^\mu$=0.7 nM, $K_i{}^\delta$=1 nM, $K_i{}^{NK1}$=4.9 nM, $K_i{}^{rNK1}$=87 nM, Table VIII) This ligand having Dmt at $1^{st}$ position and Gly at $6^{th}$ position showed two times higher agonist activity at MOR compared to that at DOR ($IC_{50}{}^\mu$=7.9 nM, $IC_{50}{}^\delta$=16 nM, $K_e{}^{NK1}$=26 nM, Table IX). Ligands AKG171, AKG172, AKG173, and AKG174, were designed and synthesized by replacing $5^{th}$ residue i.e. Ser of AKG126 by Dap, Dab, Orn, and Lys respectively. Ligands AKG171 and AKG172 showed binding selectivity at MOR over DOR (AKG171: $K_i{}^\mu$=3 nM, $K_i{}^\delta$=33 nM, $K_i{}^{hNK1}$=3 nM, $K_i{}^{rNK1}$=8.5 nM; AKG172: $K_i{}^\mu$=8 nM, $K_i{}^\delta$=100 nM, $K_i{}^{hNK1}$=3.05 nM, $K_i{}^{rNK1}$=8.2 nM; Table VIII). Surprisingly, AKG173 containing Orn as $5^{th}$ residue showed 100 times binding selectivity at DOR over MOR ($K_i{}^\mu$=5 nM, $K_i{}^\delta$=0.05 nM, $K_i{}^{hNK1}$=15.5 nM, $K_i{}^{rNK1}$=65 nM, Table VIII). All these ligands showed strong binding affinity at NK1R and the difference between hNK1R and rNK1R binding affinities became low (Table VIII). Functional assays with these ligands are in progress.

TABLE VIII

Binding affinity results at opioid and NK1 receptors

| Ligand No. | $K_i{}^\mu$ (nM) | Log[$IC_{50}\pm$] | $K_i{}^\delta$ (nM) | Log[$IC_{50}\pm$] | $K_i{}^\mu/K_i{}^\delta$ | $K_i{}^{hNK1}$ (nM) | $K_i{}^{rNK1}$ (nM) | $K_i{}^{hNK1}/K_i{}^{rNK1}$ |
|---|---|---|---|---|---|---|---|---|
| AKG038 | 127 (n = 2) | −6.60 ± 0.12 | 7 (n = 6) | −7.74 ± 0.15 | 18/1 | 1.94 ± 0.25 | 206.1 ± 14.7 | 1/106 |
| AKG039 | 116 (n = 2) | −6.66 ± 0.06 | 6 (n = 6) | −7.82 ± 0.28 | 19/1 | 1.32 ± 0.01 | 148.1 ± 9.8 | 1/112 |
| AKG101 | 196 (n = 2) | −6.35 ± 0.26 | 34 (n = 2) | −7.13 ± 0.07 | 6/1 | 2.77 ± 0.51 | 108 ± 22.6 | 1/39 |
| AKG126 | 2 (n = 2) | −8.30 ± 0.11 | 63 (n = 2) | −6.83 ± 0.05 | 1/31 | 0.86 ± 0.07 | 31.5 ± 6.64 | 1/37 |
| AKG132 | 0.4 (n = 2) | −9.03 ± 0.06 | 2 (n = 2) | −8.28 ± 0.07 | 1/5 | 5.61 ± 0.65 | 31.1 ± 5.7 | 1/6 |
| AKG133 | 8 (n = 2) | −7.69 ± 0.09 | 2 (n = 2) | −8.44 ± 0.03 | 4/1 | 4.86 ± 1.88 | 125.0 ± 40.5 | 1/26 |
| AKG134 | 2 (n = 2) | −8.27 ± 0.11 | 7 (n = 2) | −7.84 ± 0.17 | 1/4 | 7.95 ± 0.87 | 50.2 ± 16.9 | 1/6 |
| AKG135 | 0.5 (n = 2) | −8.93 ± 0.09 | 0.5 (n = 2) | −9.00 ± 0.03 | 1/1 | 7.26 ± 0.59 | 51.7 ± 16.2 | 1/7 |
| AKG-CRA-136 | 3 (n = 4) | −8.07 ± 0.18 | 38 (n = 4) | −7.07 ± 0.08 | 1/9 | 9.23 ± 1.38 | 156.0 ± 2.33 | 1/17 |
| AKC-CRA-137 | 0.7 (n = 2) | −8.82 ± 0.26 | 1 (n = 2) | −8.57 ± 0.07 | 1/1.4 | 4.76 ± 0.23 | 87.5 | 1/18 |
| AKG171 | 3 (n = 2) | −8.24 ± 0.49 | 33 (n = 2) | −7.13 ± 0.05 | 1/11 | 2.98 ± 0.36 | 8.59 ± 0.89 | 1/3 |
| AKG172 | 8 | −7.84 ± 0.11 | 100 | −6.65 ± 0.08 | 1/12 | 3.05 ± 0.33 | 8.24 ± 3.56 | 1/2.7 |
| AKG173 | 5 | −7.95 ± 0.08 | 0.05 | −6.30 ± 0.07 | 100/1 | 15.5 ± 2.03 | 65.2 ± 9.0 | 1/4.2 |
| AKG174 | 8 | −7.81 ± 0.08 | N.D. | N.D. | —/— | 3.18 ± 1.18 | 7.31 ± 0.89 | 1/2.3 |

N.D. means not determined,
n in the parenthesis indicates number of run

TABLE IX

Functional assay results

| Compd. Number | GPI (MOR) ID$_{50}$ (nM) | MVD (DOR) IC$_{50}$ (nM) | GPI/MVD IC$_{50}$ ratio | GPI/LMMP (NK1R) Agonist | $K_e$ (nM) ± S.E.M. |
|---|---|---|---|---|---|
| AKG038 | 398.7 ± 107.9 | 18.41 ± 4.37 | 21.1/1 | None at 30 nM | 4.8 ± 1.6 |
| AKG039 | 128.5 ± 20.6 | 5.988 ± 1.346 | 21.5/1 | None at 100 nM | 9.7 ± 1.3 |
| AKG101 | 39.7% at 1 uM | 6.721 ± 1.931 | —/— | None at 100 nM | 28.0 ± 11.8 |
| AKG126 | 237.3 ± 29.2 | 25.89 ± 6.69 | 9/1 | None at 30 nM | 16.53 ± 7.77 |
| AKG132 | 42.65 ± 6.00 | 7.657 ± 2.033 | 5.6/1 | None at 30 nM | 19.8 ± 2.9 |
| AKG133 | 85.40 ± 18.71 | 10.95 ± 2.50 | 7.8/1 | None at 30 nM | 2.43 ± 0.72 |
| AKG134 | 184.4 ± 30.9 | 8.936 ± 0.795 | 21/1 | None at 30 nM | 1.86 ± 0.43 |
| AKG135 | 23.45 ± 4.74 | 15.40 ± 5.40 | 2/1 | None at 100 nM | 28.7 ± 11.1 |
| AKG-CRA-136 | 108.1 ± 44.8 | 22.62 ± 2.07 | 5/1 | None at 100 nM | 27.6 ± 2.9 |
| AKG-CRA-137 | 7.871 ± 2.567 | 16.39 ± 5.17 | 1/2 | None at 100 nM | 26.3 ± 5.7 |

For every sample, the number of run was four at each receptor

In some embodiments, amide (—CONH$_2$) functionality is incorporated in the side chain of $5^{th}$ amino acid residue, and TV-methylated amino acids.

TABLE X

Physicochemical properties of the multivalent ligands

| Ligand ID | Molecular Formula | ALOGPs | HPLC RT (min) | ESI (M + H)$^+$ Obsd. | Calcd. |
|---|---|---|---|---|---|
| AKG104 | $C_{58}H_{67}F_6N_{11}O_{10}$ | 4.17 | 25.6 | 1192.1 | 1192.5055 |
| AKG102 | $C_{58}H_{67}F_6N_{11}O_{10}$ | 4.17 | 25.8 | 1192.2 | 1192.5055 |
| AKG105 | $C_{59}H_{69}F_6N_{11}O_{10}$ | 4.27 | 25.5 | 1206.3 | 1206.5211 |
| AKG103 | $C_{59}H_{69}F_6N_{11}O_{10}$ | 4.27 | 26.0 | 1206.1 | 1206.5211 |

TABLE X-continued

Physicochemical properties of the multivalent ligands

| Ligand ID | Molecular Formula | ALOGPs | HPLC RT (min) | ESI (M + H)+ Obsd. | ESI (M + H)+ Calcd. |
|---|---|---|---|---|---|
| AKG129 | $C_{60}H_{71}F_6N_{11}O_{10}$ | 4.51 | 26.3 | 1220.3 | 1220.5368 |
| AKG141 | $C_{62}H_{75}F_6N_{11}O_{10}$ | 4.74 | 25.6 | 1248.3 | 1248.5681 |
| AKG142 | $C_{59}H_{68}F_7N_{11}O_{10}$ | 4.23 | 24.8 | 1224.3 | 1224.5117 |
| AKG143 | $C_{60}H_{70}F_7N_{11}O_{10}$ | 4.48 | 25.2 | 1238.2 | 1238.5274 |
| AKG144 | $C_{62}H_{74}F_7N_{11}O_{10}$ | 4.73 | 25.9 | 1266.3 | 1266.5587 |
| AKG-SK-145 | $C_{62}H_{74}F_6N_{12}O_{11}$ | 4.08 | 24.8 | 1276.3 | 1276.5504 |
| AKG-SK-146 | $C_{64}H_{78}F_6N_{12}O_{11}$ | 4.29 | 25.3 | 1304.3 | 1304.5817 |

AKG104: (same as AKG119 except Phe'=Phe and AA=Asn);
AKG102: (same as AKG119 except Phe'=Phe and AA=4-D-Asn);
AKG105: (same as AKG119 except Phe'=Phe and AA=Gln);
AKG103: (same as AKG119 except Phe'=Phe and AA=D-Gln);
AKG129: (same as AKG119 except AA=Gln);
AKG141: (same as AKG119 except Tyr'=Dmt and AA=Gln);
AKG142: (same as AKG119 except Phe'=Phe(4-F) and AA=Gln);
AKG143: (same as AKG119 except Phe'=NMePhe(4-F) and AA=Gln);
AKG144: (same as AKG119 except Tyr'=Dmt, Phe'=NMePhe(4-F) and AA=Gln);
AKG-SK-145: (same as AKG119 except x=2 and (AA)x = Gn-Gly);
AKG-SK-146: (same as AKG119 except Tyr'=Dmt, x=2, and (AA)x is Gn-Gly).

TABLE XI

Binding affinity results at opioid and NK1 receptors

| Ligand No. | $K_i^\mu$ (nM) | Log[IC$_{50}$±] | $K_i^\delta$ (nM) | Log[IC$_{50}$±] | $K_i^\mu/K_i^\delta$ | $K_i^{hNK1}$ (nM) | $K_i^{rNK1}$ (nM) | $K_i^{hNK1}/K_i^{rNK1}$ |
|---|---|---|---|---|---|---|---|---|
| AKG104 | 51 | −6.93 ± 0.05 | 17 | 7.43 ± 0.08 | 3/1 | 1.16 ± 0.04 | 20.2 ± 0.73 | 1/17.4 |
| AKG102 | 90 | −6.68 ± 0.09 | 54 | −6.90 ± 0.06 | 1.7/1 | 2.26 ± 0.32 | 133 ± 3.5 | 1/58.8 |
| AKG105 | 38 | −7.06 ± 0.18 | 9 | −7.69 ± 0.13 | 4.2/1 | 0.92 ± 0.14 | 12.5 ± 1.3 | 1/13.6 |
| AKG103 | 116 | −6.57 ± 0.05 | 72 | −6.81 ± 0.07 | 1.6/1 | 2.71 ± 0.87 | 106 ± 42.6 | 1/39.1 |
| AKG129 | 7 | −7.84 ± 0.11 | 1 | −8.56 ± 0.04 | 7/1 | 0.83 ± 0.25 | 19.4 ± 7.7 | 1/23.4 |
| AKG141 | N.D. | N.D. | N.D. | N.D. | —/— | 4.4 ± 2.15 | 20.0 ± 1.8 | 1/10 |
| AKG142 | 8 | −7.67 ± 0.07 | 2 | −8.47 ± 0.05 | 4/1 | 5.71 ± 0.73 | 18.1 ± 1.52 | 1/3.2 |
| AKG143 | 2 | −8.35 ± 0.07 | 0.7 | −8.84 ± 0.08 | 2.9/1 | 3.2 ± 0.28 | 21.7 ± 9.1 | 1/6.8 |
| AKG144 | 0.5 | −8.94 ± 0.07 | 0.2 | −9.36 ± 0.03 | 2.5/1 | 5.39 ± 1.4 | 23.7 ± 5.9 | 1/4.2 |
| AKG-SK-145 | 2 | −8.43 ± 0.08 | 6 | −7.84 ± 0.05 | 1/3 | 7.5 ± 1.23 | 125.0 ± 13.8 | 1/16 |
| AKG-SK-146 | 0.6 | −8.94 ± 0.17 | 0.6 | −8.85 ± 0.06 | 1/1 | 6.37 ± 1.54 | 78.6 ± 9.8 | 1/15 |

N.D. means not determined,
n in the parenthesis indicates number of run

Our structure-activity relationship (SAR) study began with the ligand AKG104 in which Asn was introduced as 5$^{th}$ residue in place of Nle of TY045. It showed moderate binding affinities at all receptors ($K_i^\mu$=51 nM, $K_i^\delta$=17 nM, $K_i^{hNK1}$=1.2 nM, $K_i^{rNK1}$=20 nM, Table XI). Inversion of chirality at 5$^{th}$ residue produced ligand AKG102, which displayed inferior biological profiles at all receptors ($K_i^\mu$=90 nM, $K_i^\delta$=54 nM, $K_i^{hNK1}$=2.3 nM, $K_i^{rNK1}$=130 nM, Table XI). To examine the effect of length of side chain, Gln was introduced in place of Asn to get AKG105. It showed little better binding affinities at every receptor under study ($K_i^\mu$=38 nM, $K_i^\delta$=9 nM, $K_i^{hNK1}$=1 nM, $K_i^{rNK1}$=12 nM, TableXI). To be confirmed on the effect of inversion of chirality at 5$^{th}$ residue, D-Gln containing AKG103 was designed and synthesized. This modification reduced the affinities for all the receptors ($K_i^\mu$=120 nM, $K_i^\delta$=72 nM, $K_i^{hNK1}$=2.1 nM, $K_i^{rNK1}$=110 nM, Table XI). As better results were observed with AKG105, further structural modifications were made on it. N-methylation on 4$^{th}$ residue i.e. Phe gave the ligand AKG129. This change made the resultant ligand more potent at opioid receptors while maintaining its affinity at NK1R ($K_i^\mu$=7 nM, $K_i^\delta$=1 nM, $K_i^{hNK1}$=1 nM, $K_i^{rNK1}$=19 nM, Table XI). AKG141, which was produced because of the replacement of Tyr at position from AKG129 by Dmt, became potent at opioid receptors ($K_i^\mu$=x nM, $K_i^\delta$=x nM, $K_i^{hNK1}$=x nM, $K_i^{rNK1}$=x nM, Table XI). AKG142, a ligand containing Phe(4-F) as 4$^{th}$ residue instead of Phe as it was AKG105, became more potent ($K_i^\mu$=8 nM, $K_i^\delta$=2 nM, $K_i^{hNK1}$=5.7 nM, $K_i^{rNK1}$=18 nM, Table XI) compared to the parent ligand but furnished similar results when compared to those shown by AKG129. To examine the effect of N-methylation we introduced NMePhe(4-F) as 4$^{th}$ residue, which produced the ligand AKG143. This modification further increased the potency at opioid receptors with no significance change of that at NK1R ($K_i^\mu$=2 nM, $K_i^\delta$=0.7 nM, $K_i^{hNK1}$=3.2 nM, $K_i^{rNK1}$=22 nM, Table XI). When Dmt was introduced, though the new ligand AKG144 became more potent at opioid receptors, and it showed small decrease at NK1R ($K_i^\mu$=0.5 nM, $K_i^\delta$=0.2 nM, $K_i^{hNK1}$=5.4 nM, $K_i^{rNK1}$=24 nM, Table XI). This reduction might be due to the interference of opioid pharmacophore in the affinity of NK1 pharmacophore. In an effort to reduce this interference we increased the length of the address region by introducing Gly as $6^{th}$ residue in ligand AKG-SK-145. But, it further reduced affinities at rNK1 receptors ($K_i^\mu$=2 nM, $K_i^\delta$=6 nM, $K_i^{hNK1}$=7.5 nM, $K_i^{rNK1}$=120 nM, Table XI). Introduction of Dmt at $1^{st}$ position, which produced the ligand AKG-SK-146, provided improved potency at all receptors including rNK1 ($K_i^\mu$=0.6 nM, $K_i^\delta$=0.6 nM, $K_i^{hNK1}$=6.4 nM, $K_i^{rNK1}$=79 nM, Table XI).

Still in other embodiments, compounds having a combination of dermorphin (H-Tyr-D-Ala-Phe-Gly-Tyr-Pro-Ser-NH$_2$), a naturally occurring and highly mu-selective ligand, and NK1 derived pharmacophores are provided. For the first time, structural features of dermorphin have been introduced into the multivalent ligands. N-Methylated unnatural amino acids also have been introduced during this study.

TABLE XII

Physicochemical properties of the multivalent ligands

| Ligand ID | Molecular Formula | ALOGPs | ESI (M + H)$^+$ Obsd. | ESI (M + H)$^+$ Calcd. |
|---|---|---|---|---|
| AKG114 | $C_{63}H_{70}F_6N_{10}O_{10}$ | 5.60 | 1241.3 | 1241.5259 |
| AKG118 | $C_{65}H_{74}F_6N_{10}O_{10}$ | 5.66 | 1269.2 | 1269.5572 |
| AKG210 | $C_{64}H_{71}F_7N_{10}O_{10}$ | 5.61 | 1273.3 | 1273.5321 |
| AKG211 | $C_{64}H_{72}F_6N_{10}O_{10}$ | 5.71 | 1255.3 | 1255.5415 |
| AKG212 | $C_{64}H_{71}F_7N_{10}O_{10}$ | 5.62 | 1273.2 | 1273.5321 |
| AKG213 | $C_{64}H_{72}F_6N_{10}O_{10}$ | 5.72 | 1255.3 | 1255.5415 |
| AKG214 | $C_{66}H_{75}F_6N_{11}O_{12}$ | 4.61 | 1327.2 | 1327.5501 |
| AKG215 | $C_{71}H_{82}F_6N_{12}O_{13}$ | 4.64 | 1425.4 | 1425.6107 |

AKG114: (SEQ ID NO:32, where Tyr'=Tyr, R on Ala, Gly and Leu is H, Phe'=Phe, x=0, and XCH(R) Ph(R')$_2$ is NHCH$_2$(3,5-difluorophenyl);
AKG118: (same as AKG114 except Tyr' at position 1 is Dmt);
AKG210: (same as AKG114 except Phe'=Phe(4-F));
AKG211: (same as AKG114 except R on Gly is methyl);
AKG212: (same as AKG114 except Phe'=Phe(4-F), R on Gly is methyl);
AKG213: (same as AKG114 except Phe'=NMePhe);
AKG214: (same as AKG114 except x=1 and AA=Ser);
AKG215: (same as AKG114 except x=2 and (AA)x = Pro-Ser).

Here, we introduced the structural features of dermorphin (H-Tyr-D-Ala-Phe-Gly-Tyr-Pro-Ser-NH$_2$), a mu-selective peptide based opioid ligand. Compound AKG114 was designed by removing Ser from the C-terminal and connecting the remaining sequence of dermorphin with NK1 pharmacophore. In this ligand Pro was anticipated to influence binding affinities at opioid as well as NK1 receptors. It showed 5 times higher binding affinity for MOR compared to that for DOR and high affinity at NK1R ($K_i^\mu$=4 nM, $K_i^\delta$10=19 nM, $K_i^{hNK1}$=2 nM, $K_i^{rNK1}$=40 nM, Table XII). Functional assay with this ligand displayed 4 times higher agonist activity at DOR compared to that at MOR ($IC_{50}^\mu$=110 nM, $IC_{50}^\delta$=29 nM, $K_e^{NK1}$=15 nM, Table XIII). Replacement of $1^{st}$ residue i.e. Tyr by Dmt resulted the molecule AKG118 and it exhibited higher binding affinity at opioid receptors while maintaining that NK1R ($K_i^\mu$=1 nM, $K_i^\delta$=3 nM, $K_i^{hNK1}$=2.3 nM, $K_i^{rNK}$=25 nM, Table XII). We have designed and synthesized AKG210, AKG211, AKG212, AKG213, AKG214, and AKG215 to achieve higher selectivity for MOR over DOR. Biological studies are in progress with these molecules.

TABLE XIII

Binding affinity results at opioid and NK1 receptors

| Ligand No. | $K_i^\mu$ (nM) | Log[$IC_{50}$±] | $K_i^\delta$ (nM) | Log[$IC_{50}$±] | $K_i^\mu/K_i^\delta$ | $K_i^{hNK1}$ (nM) | $K_i^{rNK1}$ (nM) | $K_i^{hNK1}/K_i^{rNK1}$ |
|---|---|---|---|---|---|---|---|---|
| AKG114 | 4 (n = 2) | −8.02 ± 0.04 | 19 (n = 2) | −7.40 ± 0.07 | 1/5 | 1.96 ± 0.37 (n = 6) | 39.6 ± 0.41 (n = 6) | 1/22.2 |
| QXP04 | 10 (n = 2) | −7.66 ± 0.05 | 69 (n = 2) | −6.82 ± 0.06 | 1/7 | 3.8 ± 0.54 (n = 6) | 13.0 ± 1.7 (n = 6) | 1/3.4 |
| AKG118 | 1 (n = 2) | −8.65 ± 0.12 | 3 (n = 2) | −8.20 ± 0.04 | 1/3 | 2.34 ± 0.39 (n = 6) | 25.4 ± 4.17 (n = 6) | 1/11 |
| AKG210 | N.D. | N.D. | N.D. | N.D. | —/— | 3.85 ± 2.82 (n = 6) | —/— | |

N.D. means not determined,
n in the parenthesis indicates number of run

TABLE XIV

Functional assay results

| Compd. Number | GPI (MOR) $IC_{50}$ (nM) | MVD (DOR) $IC_{50}$ (nM) | GPI/MVD $IC_{50}$ ratio | GPI/LMMP (NK1R) Agonist | GPI/LMMP (NK1R) $K_e$ (nM) ± S.E.M. |
|---|---|---|---|---|---|
| AKG114 | 111.5 ± 12.8 | 28.98 ± 6.70 | 4/1 | None at 300 nM | 15.0 ± 4.2 |
| QXP04 | 389.2 ± 179.7 | 16.59 ± 4.57 | 23/1 | None at 1 uM | 36.3 ± 16.2 |

For every sample, the number of run was six at each receptor

In one embodiment, compounds having a combination of morphiceptin (H-Tyr-Pro-Phe-Pro-NH$_2$), a synthetic and highly mu-selective ligand, and NK1 derived pharmacophores are provided. For the first time, structural features of morphiceptin have been incorporated into the multivalent ligands.

TABLE XV

Physicochemical properties of the multivalent ligands

| Ligand ID | Molecular Formula | ALOGPs | HPLC RT (min) | ESI (M + H)$^+$ Obsd. | ESI (M + H)$^+$ Calcd. |
|---|---|---|---|---|---|
| AKG196 | C$_{54}$H$_{60}$F$_6$N$_8$O$_7$ | 5.84 | 26.4 | 1047.4547 | 1047.4567 |
| AKG197 | C$_{59}$H$_{67}$F$_6$N$_9$O$_8$ | 5.88 | 27.7 | 1144.5085 | 1144.5095 |
| AKG198 | C$_{62}$H$_{73}$F$_6$N$_9$O$_{10}$ | 5.99 | 27.9 | 1218.5457 | 1218.5463 |
| AKG200 | C$_{56}$H$_{63}$F$_6$N$_9$O$_8$ | 5.43 | 26.1 | 1104.4767 | 1104.4782 |
| AKG201 | C$_{57}$H$_{65}$F$_6$N$_9$O$_8$ | 5.64 | 26.0 | 1118.4949 | 1118.4939 |
| AKG202 | C$_{56}$H$_{63}$F$_6$N$_9$O$_8$ | 5.45 | 26.0 | 1104.4776 | 1104.4782 |
| AKG203 | C$_{57}$H$_{65}$F$_6$N$_9$O$_8$ | 5.64 | 26.5 | 1118.4921 | 1118.4939 |

AKG196: (SEQ ID NO:43 where Tyr'=Tyr, Z is absent, Phe'=Phe, x=0, R on Leu and Trp is H and XCH(R) Ph(R')$_2$ is NHCH$_2$(3,5-difluorophenyl);
QXP08: (same as AKG196 except R on Trp is methyl);
AKG197: (same as AKG196 except x=1 and AA=Pro);
AKG198: (same as AKG196 except x=2, (AA)x = Gly-Nle, and R on Trp is methyl);
AKG200: (same as AKG196 except x=1 and AA=Gly);
AKG201: (same as AKG196 except x=1 and AA=NMeGly);
AKG202: (SEQ ID NO:33, where Tyr'=Tyr, R on Gly and Leu is H, Phe'=Phe, x =0, and XCH(R) Ph(R')$_2$ is NHCH$_2$(3,5-difluorophenyl);
AKG203: (same as AKG202 except Phe'=NMePhe).

Here, we have designed and synthesized multivalent ligands based on the structural feature of mu-selective pharmacophore morphiceptin. AKG196, AKG197, AKG198, AKG200, AKG201, AKG202 and AKG203 have been synthesized and characterized by mass spectrometry (Table XV).

In another embodiment, structural features of endogenous opioid peptides endomorphin-1 (H-Tyr-Pro-Trp-Phe-NH$_2$) and endomorphin-2 (H-Tyr-Pro-Phe-Phe-NH$_2$) have been taken into consideration for the design of opioid pharmacophore part. For the first time, structural features of endomorphins have been incorporated into these kinds of multivalent ligands.

TABLE XVI

Physicochemical properties of the multivalent ligands

| Ligand ID | Molecular Formula | ALOGPs | ESI (M + H)$^+$ Obsd. | ESI (M + H)$^+$ Calcd. |
|---|---|---|---|---|
| AKG221 | C$_{65}$H$_{70}$F$_6$N$_{10}$O$_8$ | 5.93 | 1233.3 | 1233.5361 |
| AKG222 | C$_{63}$H$_{69}$F$_6$N$_9$O$_8$ | 6.30 | 1194.3 | 1194.5252 |
| AKG223 | C$_{66}$H$_{72}$F$_6$N$_{10}$O$_8$ | 6.23 | 1247.2 | 1247.5517 |
| AKG224 | C$_{64}$H$_{71}$F$_6$N$_9$O$_8$ | 6.58 | 1208.3 | 1208.5408 |
| AKG225 | C$_{67}$H$_{74}$F$_6$N$_{10}$O$_8$ | 6.65 | 1261.3 | 1261.5674 |
| AKG226 | C$_{65}$H$_{73}$F$_6$N$_9$O$_8$ | 6.86 | 1222.2 | 1222.5565 |
| AKG227 | C$_{72}$H$_{75}$F$_6$N$_{11}$O$_9$ | 6.17 | 1352.2 | 1352.5732 |

TABLE XVI-continued

Physicochemical properties of the multivalent ligands

| Ligand ID | Molecular Formula | ALOGPs | ESI (M + H)$^+$ Obsd. | ESI (M + H)$^+$ Calcd. |
|---|---|---|---|---|
| AKG228 | C$_{73}$H$_{77}$F$_6$N$_{11}$O$_9$ | 6.26 | 1366.3 | 1366.5888 |
| AKG229 | C$_{73}$H$_{77}$F$_6$N$_{11}$O$_9$ | 6.27 | 1366.3 | 1366.5888 |
| AKG230 | C$_{74}$H$_{79}$F$_6$N$_{11}$O$_9$ | 6.37 | 1380.2 | 1380.6045 |

AKG221: H-Tyr-Pro-Trp-Phe-Pro-Leu-Trp-NH-Bn(3',5'-(CF$_3$)$_2$) (SEQ ID NO:44);
AKG222: H-Tyr-Pro-Phe-Phe-Pro-Leu-Trp-NH-Bn(3',5'-(CF$_3$)$_2$) (SEQ ID NO:45);
AKG223: H-Tyr-Pro-Trp-NMePhe-Pro-Leu-Trp-NH-Bn(3',5'-(CF$_3$)$_2$) (SEQ ID NO:46);
AKG224: H-Tyr-Pro-Phe-NMePhe-Pro-Leu-Trp-NH-Bn(3',5'-(CF$_3$)$_2$) (SEQ ID NO:47);
AKG225: H-Tyr-Pro-NMeTrp-NMePhe-Pro-Leu-Trp-NH-Bn(3',5'-(CF$_3$)$_2$) (SEQ ID NO:48);
AKG226: H-Tyr-Pro-NMePhe-NMePhe-Pro-Leu-Trp-NH-Bn(3',5'-(CF$_3$)$_2$) (SEQ ID NO:49);
AKG227: (SEQ ID NO:43 where Tyr'=Tyr, Z=Trp, Phe'=NMePhe, x=1, AA=4-Abz, R on Leu and Trp is H and XCH(R) Ph(R')$_2$ is NHCH$_2$(3,5-difluorophenyl);
AKG228: (same as AKG227 except AA=4-Amb);
AKG229: (same as AKG227 except AA=4-Apac);
AKG230: (same as AKG227 except AA=4-Ampa).

Here, we have designed and synthesized multivalent ligands based on the structural feature of mu-selective pharmacophore endomorphins. AKG221, AKG222, AKG223, AKG224, AKG225, AKG226, AKG227, AKG228, AKG229, and AKG230 have been synthesized and characterized by mass spectrometry (TableXVII). Biological studies with these ligands are in progress.

TABLE XVII

Binding affinity results at opioid and NK1 receptors

| Ligand No. | K$_i^\mu$ (nM) | Log[IC$_{50}$±] | K$_i^\delta$ (nM) | Log[IC$_{50}$±] | K$_i^\mu$/K$_i^\delta$ | K$_i^{hNK1}$ (nM) | K$_i^{rNK1}$ (nM) | K$_i^{hNK1}$/K$_i^{rNK1}$ |
|---|---|---|---|---|---|---|---|---|
| AKG221 | N.D. | N.D. | N.D. | N.D. | —/— | 3.34 ± 0.32 (n = 6) | 38.46 ± 3.6 (n = 6) | 1/11.5 |
| AKG222 | N.D. | N.D. | N.D. | N.D. | —/— | 4.19 ± 0.82 (n = 6) | 32.4 ± 9.0 (n = 6) | 1/7.7 |
| AKG223 | N.D. | N.D. | N.D. | N.D. | —/— | 3.59 ± 0.3 (n = 6) | 10.11 ± 6.3 (n = 6) | 1/2.8 |

TABLE XVII-continued

Binding affinity results at opioid and NK1 receptors

| Ligand No. | $K_i^\mu$ (nM) | Log[IC$_{50}$±] | $K_i^\delta$ (nM) | Log[IC$_{50}$±] | $K_i^\mu/K_i^\delta$ | $K_i^{hNK1}$ (nM) | $K_i^{rNK1}$ (nM) | $K_i^{hNK1}/K_i^{rNK1}$ |
|---|---|---|---|---|---|---|---|---|
| AKG224 | N.D. | N.D. | N.D. | N.D. | —/— | 3.39 ± 0.85 (n = 6) | 33.74 ± 2.78 (n = 6) | 1/10 |
| AKG225 | N.D. | N.D. | N.D. | N.D. | —/— | 14.8 ± 1.4 (n = 6) | 301.9 ± 78.5 (n = 6) | 1/20 |
| AKG226 | N.D. | N.D. | N.D. | N.D. | —/— | 5.90 ± 0.5 (n =6) | 31.72 ± 13.3 (n = 6) | 1/5.4 |

N.D. means not determined,
n in the parenthesis indicates number of run

In Vitro Metabolic Stability

To check the stability of some of our lead ligands, we conducted metabolic stability study by incubating the ligands in rat plasma at 37° C. Ligand AKG115 ($T_{1/2}$: >24 h) and AKG127 ($T_{1/2}$: >24 h) showed significant enhancement in stability compared to both TY027 ($T_{1/2}$: 4.8 h) and TY032 ($T_{1/2}$: >6 h). Compound AKG190 was also tested for its metabolic stability to know the effect of $4^{th}$ residue. It showed lower half-life ($T_{1/2}$: <2 h) compared to that for AKG115 and AKG127. These results suggest that presence of Dmt at $1^{st}$ position is playing the main role in enhancing the metabolic stability.

In Vivo Results

Figure 4:
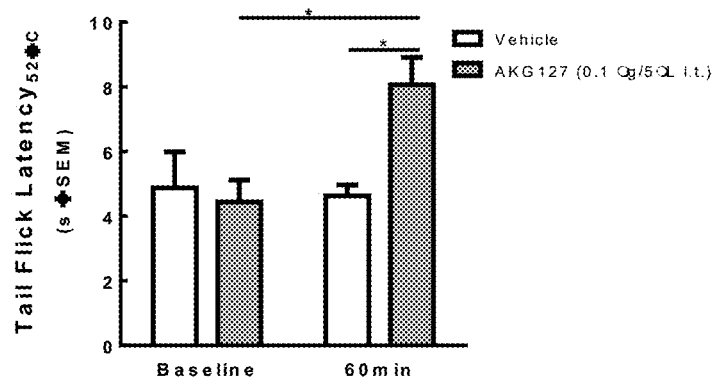
FIG. 4 shows tail flick latency after administration of AKG127 in accordance with the present invention.

Comparison of our in vitro results suggested that number of compounds including AKG115, AKG116, AKG127, AKG113, AKG-CRA-177, AKG114 and AKG118 may have antinociceptive activity in vivo. We chose compounds AKG115 and AKG127 for preliminary in vivo studies. The efficacy of spinal AKG115 (0.1 µg in 5 µL) or vehicle were evaluated in rats using a radiant heat assay to elicit a paw withdrawal reflex. Paw withdrawal latencies (PWLs) of rats given AKG115 were not significantly higher than vehicle-treated rats and baseline values 60 min after the injection (FIG. 3). The dose was increased to 10 µg in 5 µl; however, motor skills were impaired rendering analysis of PWLs inconclusive (data not shown). The structural modification made to compound AKG115 to create compound AKG127 indicated that in in vivo activity may be more pronounced in the latter. Preliminary studies in a mouse model of acute thermal pain showed that tail flick latencies (TFLs) of mice administered AKG127 (0.1 µg in 5 µl, i.t.) were significantly higher than vehicle-treated mice and baseline values 60 min after injection (p=0.04 compared to vehicle treatment group, p=0.02 compared to baseline value; FIG. 4).

Figure 5:
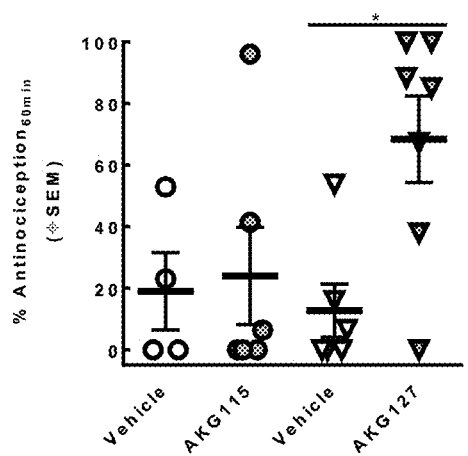
FIG. 5 shows the percentage of antinociception at the same dose for two ligands, AKG115 and AKG127.

To determine if the structural modifications significantly impacted the maximal percent activity of AKG115 and AKG127, we calculated the % antinociception (Equation1) at the same dose is shown in FIG. 5.

For both studies, maximal percent efficacy was calculated and expressed as:

$$\% \text{ Antinociception} = 100 * \frac{\text{test latency after drug treatment} - \text{baseline latency}}{\text{cutoff} - \text{baseline latency}}$$

Equation 1

Here we showed limited in vivo activity of ligands AKG115 and AKG127 in a model of acute thermal pain in two species. Despite having high binding affinity and in vitro functional activity, the maximal level of antinociception observed after AKG115 administration was minimal; in contrast, AKG127 administration was approximately 70%. These data suggest that structural modifications in the linker region of the opioid agonist/NK1 antagonist enhanced in vivo activity.

The compounds of the present invention, salts, and derivatives thereof can be incorporated into pharmaceutical compositions suitable for administration. Such compositions typically comprise the compound and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the compounds can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Opiod Agonist

<400> SEQUENCE: 1

Tyr Gly Gly Phe Met
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: Opioid Agonist

<400> SEQUENCE: 2

Thr Gly Gly Phe Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Opioid Agonist
<220> FEATURE:
<221> NAME/KEY: MISC_FEATURE
<222> LOCATION: (2)..(2)
<223> OTHER INFORMATION: D-Isomer
<220> FEATURE:
<221> NAME/KEY: MISC_FEATURE
<222> LOCATION: (4)..(4)
<223> OTHER INFORMATION: Amino group is methylated.
<220> FEATURE:
<221> NAME/KEY: MISC_FEATURE
<222> LOCATION: (5)..(5)
<223> OTHER INFORMATION: Carboxylic Acid group (-CO2H) is reduced to
      hydroxyl group (-OH)

<400> SEQUENCE: 3

Thr Ala Gly Phe Gly
1               5

<210> SEQ ID NO 4
<211> LENGTH: 7
<212> TYPE: PRT
<213> ORGANISM: Artificial Sequence
<220> FEATURE:
<223> OTHER INFORMATION: Opioid Agonist
<220> FEATURE:
<221> NAME/KEY: MISC_FEATURE
<222> LOCATION: (2)..(2)
<223> OTHER INFORMATION: D-Isomer
<220> FEATURE:
<221> NAME/KEY: MISC_FEATURE
<222> LOCATION: (7)..(7)
<223> OTHER INFORMATION: Carboxylic Acid (-CO2H) is replaced with Amide
      group (-CONH2)

<400> SEQUENCE: 4

Thr Ala Phe Gly Thr Pro Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Opioid Agonist
<220> FEATURE:
<221> NAME/KEY: MISC_FEATURE
<222> LOCATION: (4)..(4)
<223> OTHER INFORMATION: Carboxylic acid group is replaced with an amide
      group

<400> SEQUENCE: 5

Thr Pro Phe Pro
1
```

```
<210> SEQ ID NO 6
<211> LENGTH: 4
<212> TYPE: PRT
<213> ORGANISM: Artificial Sequence
<220> FEATURE:
<223> OTHER INFORMATION: Opioid Agonist
<220> FEATURE:
<221> NAME/KEY: MISC_FEATURE
<222> LOCATION: (4)..(4)
<223> OTHER INFORMATION: Carboxylic acid is replaced with an amide group

<400> SEQUENCE: 6

Thr Pro Trp Phe
1

<210> SEQ ID NO 7
<211> LENGTH: 4
<212> TYPE: PRT
<213> ORGANISM: Artificial Sequence
<220> FEATURE:
<223> OTHER INFORMATION: Opioid Agonist
<220> FEATURE:
<221> NAME/KEY: MISC_FEATURE
<222> LOCATION: (4)..(4)
<223> OTHER INFORMATION: Carboxylic acid group is replaced with an amide
      group.

<400> SEQUENCE: 7

Thr Pro Phe Phe
1

<210> SEQ ID NO 8
<211> LENGTH: 8
<212> TYPE: PRT
<213> ORGANISM: Artificial Sequence
<220> FEATURE:
<223> OTHER INFORMATION: NK1 antagonist
<220> FEATURE:
<221> NAME/KEY: MISC_FEATURE
<222> LOCATION: (2)..(2)
<223> OTHER INFORMATION: D-Isomer
<220> FEATURE:
<221> NAME/KEY: MISC_FEATURE
<222> LOCATION: (8)..(8)
<223> OTHER INFORMATION: Carboxylic acid (-CO2H) is replaced with an
      amide group (-CONHR, where R is substituted with 3',5'-
      ditrifluoromethylbenzyl)

<400> SEQUENCE: 8

Thr Ala Gly Phe Met Pro Leu Trp
1               5

<210> SEQ ID NO 9
<211> LENGTH: 8
<212> TYPE: PRT
<213> ORGANISM: Artificial Sequence
<220> FEATURE:
<223> OTHER INFORMATION: TY005
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (8)..(8)
<223> OTHER INFORMATION: Carboxylic acid (-CO2H) is replaced with
      -COONHR, where R is 3',5'-ditrifluoromethylbenzyl

<400> SEQUENCE: 9

Thr Ala Gly Phe Met Pro Leu Trp
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Peptide #10
<220> FEATURE:
<221> NAME/KEY: MISC_FEATURE
<222> LOCATION: (1)..(1)
<223> OTHER INFORMATION: Tyr and its derivatives, e.g., Dmt etc.
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: alpha-amino group is optionally substituted
      with an alkyl such as methyl
<220> FEATURE:
<221> NAME/KEY: MISC_FEATURE
<222> LOCATION: (3)..(3)
<223> OTHER INFORMATION: alpha-amino group is optionally substituted
      with an alkyl such as methyl
<220> FEATURE:
<221> NAME/KEY: MISC_FEATURE
<222> LOCATION: (4)..(4)
<223> OTHER INFORMATION: Phe and its derivatives, e.g., NMePhe,
      Phe(4-F), etc.
<220> FEATURE:
<221> NAME/KEY: MISC_FEATURE
<222> LOCATION: (6)..(6)
<223> OTHER INFORMATION: alpha-amino group is optionally substituted
      with an alkyl such as methyl
<220> FEATURE:
<221> NAME/KEY: MISC_FEATURE
<222> LOCATION: (7)..(7)
<223> OTHER INFORMATION: alpha-amino group is optionally substituted
      with an alkyl such as methyl
<220> FEATURE:
<221> NAME/KEY: MISC_FEATURE
<222> LOCATION: (7)..(7)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with H,
      CH3, etc.

<400> SEQUENCE: 10

Xaa Ala Gly Xaa Pro Leu Trp
1               5

<210> SEQ ID NO 11
<211> LENGTH: 7
<212> TYPE: PRT
<213> ORGANISM: Artificial Sequence
<220> FEATURE:
<223> OTHER INFORMATION: Compound of the invention
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 11

Tyr Ala Gly Phe Pro Leu Trp
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Compound 12
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 12

Xaa Ala Gly Phe Pro Leu Trp
1               5

<210> SEQ ID NO 13
<211> LENGTH: 7
<212> TYPE: PRT
<213> ORGANISM: Artificial Sequence
<220> FEATURE:
<223> OTHER INFORMATION: Compound 13
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 13

Xaa Ala Gly Phe Pro Leu Trp
1               5

<210> SEQ ID NO 14
<211> LENGTH: 7
<212> TYPE: PRT
<213> ORGANISM: Artificial Sequence
<220> FEATURE:
<223> OTHER INFORMATION: Compound 14
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with fluoride
<220> FEATURE:
<221> NAME/KEY: MISC_FEATURE
```

```
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 14

Xaa Ala Gly Phe Pro Leu Trp
1               5

<210> SEQ ID NO 15
<211> LENGTH: 7
<212> TYPE: PRT
<213> ORGANISM: Artificial Sequence
<220> FEATURE:
<223> OTHER INFORMATION: Compound 15
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with fluoride
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 15

Xaa Ala Gly Phe Pro Leu Trp
1               5

<210> SEQ ID NO 16
<211> LENGTH: 7
<212> TYPE: PRT
<213> ORGANISM: Artificial Sequence
<220> FEATURE:
<223> OTHER INFORMATION: Compound 16
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with chloride
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 16

Xaa Ala Gly Phe Pro Leu Trp
1               5

<210> SEQ ID NO 17
<211> LENGTH: 7
<212> TYPE: PRT
```

```
<213> ORGANISM: Artificial Sequence
<220> FEATURE:
<223> OTHER INFORMATION: Compound 17
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with bromide
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 17

Xaa Ala Gly Phe Pro Leu Trp
1               5

<210> SEQ ID NO 18
<211> LENGTH: 7
<212> TYPE: PRT
<213> ORGANISM: Artificial Sequence
<220> FEATURE:
<223> OTHER INFORMATION: Compound 18
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with iodide
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 18

Xaa Ala Gly Phe Pro Leu Trp
1               5

<210> SEQ ID NO 19
<211> LENGTH: 10
<212> TYPE: PRT
<213> ORGANISM: Artificial Sequence
<220> FEATURE:
<223> OTHER INFORMATION: Compound 19 (General Structure)
<220> FEATURE:
<221> NAME/KEY: MISC_FEATURE
<222> LOCATION: (1)..(1)
<223> OTHER INFORMATION: Tyr and its derivatives, e.g., Dmt etc.
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: alpha-amino group is optionally substituted
      with alkyl, such as methyl, etc.
<220> FEATURE:
```

```
<221> NAME/KEY: MISC_FEATURE
<222> LOCATION: (3)..(3)
<223> OTHER INFORMATION: alpha-amino group is optionally substituted
      with alkyl, such as methyl, etc.
<220> FEATURE:
<221> NAME/KEY: MISC_FEATURE
<222> LOCATION: (4)..(4)
<223> OTHER INFORMATION: Phe and its derivatives, e.g., NMePhe, Phe(4-F)
      etc.
<220> FEATURE:
<221> NAME/KEY: MISC_FEATURE
<222> LOCATION: (5)..(7)
<223> OTHER INFORMATION: each amino acid is independently
      natual/unnatural amino acid, e.g., Nle, Gly, beta-Ala, 4-Abu, Ahx,
      4-Amb, 4-Abz, 4-Apac, 4-Ampa etc.
<220> FEATURE:
<221> NAME/KEY: MISC_FEATURE
<222> LOCATION: (9)..(9)
<223> OTHER INFORMATION: alpha-amino group is optionally substituted
      with alkyl, such as methyl, etc.
<220> FEATURE:
<221> NAME/KEY: MISC_FEATURE
<222> LOCATION: (10)..(10)
<223> OTHER INFORMATION: alpha-amino group is optionally substituted
      with alkyl, such as methyl, etc.
<220> FEATURE:
<221> NAME/KEY: MISC_FEATURE
<222> LOCATION: (10)..(10)
<223> OTHER INFORMATION: Carboxy group (-CO2H) is replaced with -CONHR,
      where R is 3',5'-ditrifluoromethylbenzyl
<220> FEATURE:
<221> NAME/KEY: MISC_FEATURE
<222> LOCATION: (10)..(10)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with H,
      CH3, etc.

<400> SEQUENCE: 19

Xaa Ala Gly Xaa Xaa Xaa Xaa Pro Leu Trp
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Compound 20
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 20

Tyr Ala Gly Phe Xaa Pro Leu Trp
1               5

<210> SEQ ID NO 21
<211> LENGTH: 8
<212> TYPE: PRT
<213> ORGANISM: Artificial Sequence
```

-continued

```
<220> FEATURE:
<223> OTHER INFORMATION: Compound 21
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 21

Tyr Ala Gly Phe Gly Pro Leu Trp
1               5

<210> SEQ ID NO 22
<211> LENGTH: 8
<212> TYPE: PRT
<213> ORGANISM: Artificial Sequence
<220> FEATURE:
<223> OTHER INFORMATION: Compound 22
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with fluoride
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 22

Tyr Ala Gly Phe Gly Pro Leu Trp
1               5

<210> SEQ ID NO 23
<211> LENGTH: 8
<212> TYPE: PRT
<213> ORGANISM: Artificial Sequence
<220> FEATURE:
<223> OTHER INFORMATION: Compound 23
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (4)..(4)
<223> OTHER INFORMATION: 4-position of the phenyl group of the
      phenylalanine is substituted with fluoride
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 23

Tyr Ala Gly Phe Gly Pro Leu Trp
1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Compound 24
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: beta-alanine
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 24

Tyr Ala Gly Phe Xaa Pro Leu Trp
1               5

<210> SEQ ID NO 25
<211> LENGTH: 8
<212> TYPE: PRT
<213> ORGANISM: Artificial Sequence
<220> FEATURE:
<223> OTHER INFORMATION: Compound 25
<220> FEATURE:
<221> NAME/KEY: MISC_FEATURE
<222> LOCATION: (2)..(2)
<223> OTHER INFORMATION: D-Isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: gamma-Abu
<220> FEATURE:
<221> NAME/KEY: MISC_FEATURE
<222> LOCATION: (8)..(8)
<223> OTHER INFORMATION: gamma-AbuCarboxy group (-CO2H) is replaced with
      -CONHR, where R is 3',5'-ditrifluoromethylbenzyl

<400> SEQUENCE: 25

Tyr Ala Gly Phe Xaa Pro Leu Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Compound 26
<220> FEATURE:
<221> NAME/KEY: MISC_FEATURE
<222> LOCATION: (2)..(2)
<223> OTHER INFORMATION: D-Isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: 6-Ahx
```

```
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 26

Tyr Ala Gly Phe Xaa Pro Leu Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Compound 27
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: 4-Amb
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 27

Tyr Ala Gly Phe Xaa Pro Leu Trp
1               5

<210> SEQ ID NO 28
<211> LENGTH: 8
<212> TYPE: PRT
<213> ORGANISM: Artificial Sequence
<220> FEATURE:
<223> OTHER INFORMATION: Compound 28
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: 4-Abz
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 28

Tyr Ala Gly Phe Xaa Pro Leu Trp
1               5

<210> SEQ ID NO 29
<211> LENGTH: 8
<212> TYPE: PRT
<213> ORGANISM: Artificial Sequence
<220> FEATURE:
<223> OTHER INFORMATION: Compound 29
<220> FEATURE:
```

```
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: 4-Apac
<220> FEATURE:
<221> NAME/KEY: MISC_FEATURE
<222> LOCATION: (8)..(8)
<223> OTHER INFORMATION: 4-ApacCarboxy group (-CO2H) is replaced with
      -CONHR, where R is 3',5'-ditrifluoromethylbenzyl

<400> SEQUENCE: 29

Tyr Ala Gly Phe Xaa Pro Leu Trp
1               5

<210> SEQ ID NO 30
<211> LENGTH: 8
<212> TYPE: PRT
<213> ORGANISM: Artificial Sequence
<220> FEATURE:
<223> OTHER INFORMATION: Compound 30
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (5)..(5)
<223> OTHER INFORMATION: 4-Ampa
<220> FEATURE:
<221> NAME/KEY: MISC_FEATURE
<222> LOCATION: (8)..(8)
<223> OTHER INFORMATION: 4-AmpaCarboxy group (-CO2H) is replaced with
      -CONHR, where R is 3',5'-ditrifluoromethylbenzyl

<400> SEQUENCE: 30

Tyr Ala Gly Phe Xaa Pro Leu Trp
1               5

<210> SEQ ID NO 31
<211> LENGTH: 10
<212> TYPE: PRT
<213> ORGANISM: Artificial Sequence
<220> FEATURE:
<223> OTHER INFORMATION: General Structure 31
<220> FEATURE:
<221> NAME/KEY: MISC_FEATURE
<222> LOCATION: (1)..(1)
<223> OTHER INFORMATION: Tyr and its derivatives e.g., Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (3)..(3)
<223> OTHER INFORMATION: alpha-amino group is optionally substituted
      with methyl
<220> FEATURE:
<221> NAME/KEY: MISC_FEATURE
<222> LOCATION: (4)..(4)
<223> OTHER INFORMATION: 4-position of the phenyl group of the
      phenylalanine is optionally substituted with fluoride and alpha-
      amino group is optionally substitued with methyl
<220> FEATURE:
```

```
<221> NAME/KEY: MISC_FEATURE
<222> LOCATION: (5)..(7)
<223> OTHER INFORMATION: can be absent provided at least one is present
      and each is indenependently Ser, D-Ser, Homo-Ser, Lys, Orn, Dab,
      Dap, Ser-4-Apac, Asn, D-Asn, Gln, D-Gln, Gln-4-Apac
<220> FEATURE:
<221> NAME/KEY: MISC_FEATURE
<222> LOCATION: (9)..(9)
<223> OTHER INFORMATION: alpha-amino group is optionally substituted
      with methyl
<220> FEATURE:
<221> NAME/KEY: MISC_FEATURE
<222> LOCATION: (10)..(10)
<223> OTHER INFORMATION: alpha-amino group is optionally substituted
      with methyl
<220> FEATURE:
<221> NAME/KEY: MISC_FEATURE
<222> LOCATION: (10)..(10)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with CH3,
      etc.

<400> SEQUENCE: 31

Xaa Ala Gly Xaa Xaa Xaa Xaa Pro Leu Trp
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Generic Structure 32
<220> FEATURE:
<221> NAME/KEY: MISC_FEATURE
<222> LOCATION: (1)..(1)
<223> OTHER INFORMATION: Tyr and its derivatives, e.g., Dmt etc.
<220> FEATURE:
<221> NAME/KEY: MISC_FEATURE
<222> LOCATION: (2)..(2)
<223> OTHER INFORMATION: D-isomer and alpha-amino group is optionally
      substituted with methyl etc.
<220> FEATURE:
<221> NAME/KEY: MISC_FEATURE
<222> LOCATION: (3)..(3)
<223> OTHER INFORMATION: Phe and its derivatives, e.g., NMePhe,
      Phe(4-F), etc.
<220> FEATURE:
<221> NAME/KEY: MISC_FEATURE
<222> LOCATION: (4)..(4)
<223> OTHER INFORMATION: alpha-amino group is optionally substituted
      with methyl etc.
<220> FEATURE:
<221> NAME/KEY: MISC_FEATURE
<222> LOCATION: (5)..(5)
<223> OTHER INFORMATION: Tyr and its derivatives, e.g., Dmt etc.
<220> FEATURE:
<221> NAME/KEY: MISC_FEATURE
<222> LOCATION: (6)..(8)
<223> OTHER INFORMATION: each is independently (1) can be absent or (2)
      is indpendently natural/unnatural amino acid, e.g., 4-Amb, 4-Apac,
      Lys, etc.; X=NH, NMe, etc.
<220> FEATURE:
<221> NAME/KEY: MISC_FEATURE
<222> LOCATION: (10)..(10)
<223> OTHER INFORMATION: alpha-amino group is optionally substituted
      with methyl, etc.
<220> FEATURE:
<221> NAME/KEY: MISC_FEATURE
<222> LOCATION: (11)..(11)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with CH3,
      etc.
```

```
<400> SEQUENCE: 32

Xaa Ala Xaa Gly Xaa Xaa Xaa Xaa Pro Leu Trp
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Generic Structure 33
<220> FEATURE:
<221> NAME/KEY: MISC_FEATURE
<222> LOCATION: (1)..(1)
<223> OTHER INFORMATION: Tyr and its derivatives e.g., Dmt etc.
<220> FEATURE:
<221> NAME/KEY: MISC_FEATURE
<222> LOCATION: (3)..(3)
<223> OTHER INFORMATION: R is H, Me, etc.
<220> FEATURE:
<221> NAME/KEY: MISC_FEATURE
<222> LOCATION: (4)..(4)
<223> OTHER INFORMATION: Phe and its derivatives, e.g., NMePhe, Phe(4-F)
      etc.
<220> FEATURE:
<221> NAME/KEY: MISC_FEATURE
<222> LOCATION: (5)..(7)
<223> OTHER INFORMATION: each is independently natural/unnatural amino
      acid e.g., AA[[=AA]]=4-Amb, 4-Apac, Lys, etc.
<220> FEATURE:
<221> NAME/KEY: MISC_FEATURE
<222> LOCATION: (8)..(8)
<223> OTHER INFORMATION: R is H, Me etc.
<220> FEATURE:
<221> NAME/KEY: MISC_FEATURE
<222> LOCATION: (9)..(9)
<223> OTHER INFORMATION: R is H, Me etc.
<220> FEATURE:
<221> NAME/KEY: MISC_FEATURE
<222> LOCATION: (10)..(10)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with H,
      CH3, etc.

<400> SEQUENCE: 33

Xaa Pro Gly Xaa Xaa Xaa Xaa Pro Leu Trp
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Compound 34
<220> FEATURE:
<221> NAME/KEY: MISC_FEATURE
<222> LOCATION: (6)..(6)
<223> OTHER INFORMATION: Carboxy group (-CO2H) is replaced with -CONHR,
      where R is 3',5'-ditrifluoromethylbenzyl

<400> SEQUENCE: 34

Thr Pro Phe Pro Leu Trp
1               5

<210> SEQ ID NO 35
<211> LENGTH: 7
<212> TYPE: PRT
<213> ORGANISM: Artificial Sequence
<220> FEATURE:
<223> OTHER INFORMATION: Compound 35
<220> FEATURE:
<221> NAME/KEY: MISC_FEATURE
```

```
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 35

Tyr Pro Phe Pro Pro Leu Trp
1               5

<210> SEQ ID NO 36
<211> LENGTH: 8
<212> TYPE: PRT
<213> ORGANISM: Artificial Sequence
<220> FEATURE:
<223> OTHER INFORMATION: Compound 36
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 36

Tyr Pro Phe Gly Xaa Pro Leu Trp
1               5

<210> SEQ ID NO 37
<211> LENGTH: 8
<212> TYPE: PRT
<213> ORGANISM: Artificial Sequence
<220> FEATURE:
<223> OTHER INFORMATION: Compound 37
<220> FEATURE:
<221> NAME/KEY: MISC_FEATURE
<222> LOCATION: (5)..(5)
<223> OTHER INFORMATION: 4-Amb
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 37

Tyr Pro Phe Pro Xaa Pro Leu Trp
1               5

<210> SEQ ID NO 38
<211> LENGTH: 8
<212> TYPE: PRT
<213> ORGANISM: Artificial Sequence
<220> FEATURE:
<223> OTHER INFORMATION: Compound 38
<220> FEATURE:
<221> NAME/KEY: MISC_FEATURE
<222> LOCATION: (5)..(5)
<223> OTHER INFORMATION: 4-Amb
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 38

Tyr Pro Phe Pro Xaa Pro Leu Trp
1               5

<210> SEQ ID NO 39
<211> LENGTH: 7
<212> TYPE: PRT
```

```
<213> ORGANISM: Artificial Sequence
<220> FEATURE:
<223> OTHER INFORMATION: Compound 39
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 39

Tyr Pro Phe Gly Pro Leu Trp
1               5

<210> SEQ ID NO 40
<211> LENGTH: 7
<212> TYPE: PRT
<213> ORGANISM: Artificial Sequence
<220> FEATURE:
<223> OTHER INFORMATION: Compound 40
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 40

Tyr Pro Phe Gly Pro Leu Trp
1               5

<210> SEQ ID NO 41
<211> LENGTH: 7
<212> TYPE: PRT
<213> ORGANISM: Artificial Sequence
<220> FEATURE:
<223> OTHER INFORMATION: Compound 41
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 41

Tyr Pro Gly Phe Pro Leu Trp
1               5

<210> SEQ ID NO 42
<211> LENGTH: 7
<212> TYPE: PRT
<213> ORGANISM: Artificial Sequence
<220> FEATURE:
<223> OTHER INFORMATION: Compound 42
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 42

Tyr Pro Gly Phe Pro Leu Trp
1               5

<210> SEQ ID NO 43
<211> LENGTH: 10
```

```
<212> TYPE: PRT
<213> ORGANISM: Artificial Sequence
<220> FEATURE:
<223> OTHER INFORMATION: Generic Structure 43
<220> FEATURE:
<221> NAME/KEY: MISC_FEATURE
<222> LOCATION: (1)..(1)
<223> OTHER INFORMATION: Tyr or its derivative e.g., Dmt etc.
<220> FEATURE:
<221> NAME/KEY: MISC_FEATURE
<222> LOCATION: (3)..(3)
<223> OTHER INFORMATION: Phe or its derivative, e.g., NMePhe, Phe(4-F)
      etc. or Trp or its derivative, e.g., NMeTrp etc.
<220> FEATURE:
<221> NAME/KEY: MISC_FEATURE
<222> LOCATION: (4)..(4)
<223> OTHER INFORMATION: Phe or its derivative, e.g., NMePhe, Phe(4-F)
      etc.
<220> FEATURE:
<221> NAME/KEY: MISC_FEATURE
<222> LOCATION: (5)..(7)
<223> OTHER INFORMATION: each is independently natural/unnatural amino
      acid., e.g., AA=4-Amb, 4-Apac, Lys, etc.
<220> FEATURE:
<221> NAME/KEY: MISC_FEATURE
<222> LOCATION: (9)..(9)
<223> OTHER INFORMATION: R = H, Me etc.
<220> FEATURE:
<221> NAME/KEY: MISC_FEATURE
<222> LOCATION: (10)..(10)
<223> OTHER INFORMATION: R = H, Me etc.
<220> FEATURE:
<221> NAME/KEY: MISC_FEATURE
<222> LOCATION: (10)..(10)
<223> OTHER INFORMATION: Carboxy terminal group (-CO2H) is replaced with
      -CONR, where R is benzyl which is optionally substituted in 3'-,
      and 5'- position of the phenyl ring with H, CH3, CF3, etc. and the
      methylene group of the benzyl is optionally substituted with H,
      CH3, etc.

<400> SEQUENCE: 43

Xaa Pro Xaa Xaa Xaa Xaa Xaa Pro Leu Trp
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Compound 44
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 44

Tyr Pro Trp Phe Pro Leu Trp
1               5

<210> SEQ ID NO 45
<211> LENGTH: 7
<212> TYPE: PRT
<213> ORGANISM: Artificial Sequence
<220> FEATURE:
<223> OTHER INFORMATION: Compound 45
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 45

Tyr Pro Phe Phe Pro Leu Trp
```

<210> SEQ ID NO 46
<211> LENGTH: 7
<212> TYPE: PRT
<213> ORGANISM: Artificial Sequence
<220> FEATURE:
<223> OTHER INFORMATION: Compound 46
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 46

Tyr Pro Trp Phe Pro Leu Trp
1               5

<210> SEQ ID NO 47
<211> LENGTH: 7
<212> TYPE: PRT
<213> ORGANISM: Artificial Sequence
<220> FEATURE:
<223> OTHER INFORMATION: Compound 47
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 47

Tyr Pro Phe Phe Pro Leu Trp
1               5

<210> SEQ ID NO 48
<211> LENGTH: 7
<212> TYPE: PRT
<213> ORGANISM: Artificial Sequence
<220> FEATURE:
<223> OTHER INFORMATION: Compound 48
<220> FEATURE:
<221> NAME/KEY: MISC_FEATURE
<222> LOCATION: (3)..(3)
<223> OTHER INFORMATION: alpha-amino group is substituted with methyl
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 48

Tyr Pro Trp Phe Pro Leu Trp
1               5

<210> SEQ ID NO 49
<211> LENGTH: 7
<212> TYPE: PRT
<213> ORGANISM: Artificial Sequence
<220> FEATURE:
<223> OTHER INFORMATION: Compound 49

```
<220> FEATURE:
<221> NAME/KEY: MISC_FEATURE
<222> LOCATION: (3)..(3)
<223> OTHER INFORMATION: alpha-amino group is substituted with methyl
<220> FEATURE:
<221> NAME/KEY: MISC_FEATURE
<222> LOCATION: (4)..(4)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 49

Tyr Pro Phe Phe Pro Leu Trp
1               5

<210> SEQ ID NO 50
<211> LENGTH: 7
<212> TYPE: PRT
<213> ORGANISM: Artificial Sequence
<220> FEATURE:
<223> OTHER INFORMATION: Compound 50
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 50

Tyr Ala Gly Phe Pro Leu Trp
1               5

<210> SEQ ID NO 51
<211> LENGTH: 6
<212> TYPE: PRT
<213> ORGANISM: Artificial Sequence
<220> FEATURE:
<223> OTHER INFORMATION: Compound 51
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (6)..(6)
<223> OTHER INFORMATION: Carboxy group (-CO2H) is replaced with -CONHR,
      where R is 3',5'-ditrifluoromethylbenzyl

<400> SEQUENCE: 51

Tyr Ala Phe Pro Leu Trp
1               5

<210> SEQ ID NO 52
<211> LENGTH: 7
<212> TYPE: PRT
<213> ORGANISM: Artificial Sequence
<220> FEATURE:
<223> OTHER INFORMATION: AKG190
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group of the
      phenylalanine is substituted with fluoride
```

-continued

```
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 52

Tyr Ala Gly Phe Pro Leu Trp
1               5

<210> SEQ ID NO 53
<211> LENGTH: 7
<212> TYPE: PRT
<213> ORGANISM: Artificial Sequence
<220> FEATURE:
<223> OTHER INFORMATION: AKG180
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (3)..(3)
<223> OTHER INFORMATION: alpha-amino group is substituted with methyl
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 53

Xaa Ala Gly Phe Pro Leu Trp
1               5

<210> SEQ ID NO 54
<211> LENGTH: 7
<212> TYPE: PRT
<213> ORGANISM: Artificial Sequence
<220> FEATURE:
<223> OTHER INFORMATION: AKG181
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 54

Xaa Ala Gly Phe Pro Leu Trp
1               5

<210> SEQ ID NO 55
<211> LENGTH: 7
<212> TYPE: PRT
<213> ORGANISM: Artificial Sequence
<220> FEATURE:
<223> OTHER INFORMATION: AKG182
<220> FEATURE:
<221> NAME/KEY: MISC_FEATURE
<222> LOCATION: (1)..(1)
<223> OTHER INFORMATION: Dmt
<220> FEATURE:
```

```
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (3)..(3)
<223> OTHER INFORMATION: alpha-amino acid group is methylated
<220> FEATURE:
<221> NAME/KEY: MISC_FEATURE
<222> LOCATION: (4)..(4)
<223> OTHER INFORMATION: alpha-amino acid group is methylated
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 55

Xaa Ala Gly Phe Pro Leu Trp
1               5

<210> SEQ ID NO 56
<211> LENGTH: 7
<212> TYPE: PRT
<213> ORGANISM: Artificial Sequence
<220> FEATURE:
<223> OTHER INFORMATION: AKG183
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: alpha-amino group is methlated
<220> FEATURE:
<221> NAME/KEY: MISC_FEATURE
<222> LOCATION: (3)..(3)
<223> OTHER INFORMATION: alpha-amino group is methlated
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 56

Xaa Ala Gly Phe Pro Leu Trp
1               5

<210> SEQ ID NO 57
<211> LENGTH: 7
<212> TYPE: PRT
<213> ORGANISM: Artificial Sequence
<220> FEATURE:
<223> OTHER INFORMATION: AKG184
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: alpha-amino group is methylated
<220> FEATURE:
<221> NAME/KEY: MISC_FEATURE
<222> LOCATION: (4)..(4)
<223> OTHER INFORMATION: alpha-amino group is methylated
```

```
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 57

Xaa Ala Gly Phe Pro Leu Trp
1               5

<210> SEQ ID NO 58
<211> LENGTH: 7
<212> TYPE: PRT
<213> ORGANISM: Artificial Sequence
<220> FEATURE:
<223> OTHER INFORMATION: AKG185
<220> FEATURE:
<221> NAME/KEY: MISC_FEATURE
<222> LOCATION: (1)..(1)
<223> OTHER INFORMATION: Dmt
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (2)..(2)
<223> OTHER INFORMATION: alpha-amino group is methylated
<220> FEATURE:
<221> NAME/KEY: MISC_FEATURE
<222> LOCATION: (3)..(3)
<223> OTHER INFORMATION: alpha-amino group is methylated
<220> FEATURE:
<221> NAME/KEY: MISC_FEATURE
<222> LOCATION: (4)..(4)
<223> OTHER INFORMATION: alpha-amino group is methylated
<220> FEATURE:
<221> NAME/KEY: MISC_FEATURE
<222> LOCATION: (7)..(7)
<223> OTHER INFORMATION: Carboxy group (-CO2H) is replaced with -CONHR,
      where R is 3',5'-ditrifluoromethylbenzyl

<400> SEQUENCE: 58

Xaa Ala Gly Phe Pro Leu Trp
1               5

<210> SEQ ID NO 59
<211> LENGTH: 8
<212> TYPE: PRT
<213> ORGANISM: Artificial Sequence
<220> FEATURE:
<223> OTHER INFORMATION: TY045
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 59

Tyr Ala Gly Phe Xaa Pro Leu Thr
1               5

<210> SEQ ID NO 60
<211> LENGTH: 8
<212> TYPE: PRT
```

```
<213> ORGANISM: Artificial Sequence
<220> FEATURE:
<223> OTHER INFORMATION: AKG112
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is methylated
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 60

Tyr Ala Gly Phe Xaa Pro Leu Trp
1               5

<210> SEQ ID NO 61
<211> LENGTH: 8
<212> TYPE: PRT
<213> ORGANISM: Artificial Sequence
<220> FEATURE:
<223> OTHER INFORMATION: AKG113
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: alpha-amino group is methylated
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 61

Tyr Ala Gly Phe Gly Pro Leu Trp
1               5

<210> SEQ ID NO 62
<211> LENGTH: 8
<212> TYPE: PRT
<213> ORGANISM: Artificial Sequence
<220> FEATURE:
<223> OTHER INFORMATION: AKG130
<220> FEATURE:
<221> NAME/KEY: MISC_FEATURE
<222> LOCATION: (2)..(2)
<223> OTHER INFORMATION: D-isomer
<220> FEATURE:
<221> NAME/KEY: MISC_FEATURE
<222> LOCATION: (4)..(4)
<223> OTHER INFORMATION: 4-position of the phenyl group is substituted
      with fluoride
<220> FEATURE:
<221> NAME/KEY: MISC_FEATURE
<222> LOCATION: (8)..(8)
<223> OTHER INFORMATION: Carboxy group (-CO2H) is replaced with -CONHR,
      where R is 3',5'-ditrifluoromethylbenzyl

<400> SEQUENCE: 62

Tyr Ala Gly Phe Gly Pro Leu Trp
1               5
```

The invention claimed is:

1. A compound comprising an opioid receptor agonist moiety that is linked to a NK1 receptor antagonist moiety, wherein said compound is of the formula:

A-B wherein A is said opioid receptor agonist moiety, and wherein B is said NK1 receptor antagonist moiety of the formula:

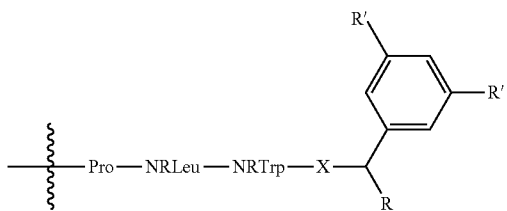

and wherein said opioid receptor agonist moiety A is a moiety of the formula:

H-Tyr'-D-NRAla-NRGly-Phe'-[AA]$_a$-, wherein
   each of R' is independently H, CH$_3$, or CF$_3$;
   X is NH or NMe;
   a is 0 or 1;
   AA is Nle, β-Ala, γ-Abu, Ahx, 4-Amb, 4-Abz, 4-Apac, or 4-Ampa;
   Tyr' is Tyr or Dmt;
   Phe' is N-methylated Phe, or Phe(4-F); and
   R is H or methyl provided at least one of R on said opioid receptor agonist is methyl or Phe' is N-methylated Phe.

2. The compound of according to claim 1, wherein Tyr' is Tyr.

3. The compound according to claim 1, wherein Tyr' is Dmt.

4. The compound according to claim 1, Phe' is N-methylated Phe.

5. The compound according to claim 1, wherein a is 0.

6. The compound according to claim 1, wherein a is 1.

7. The compound according to claim 6, wherein AA is Nle.

8. The compound according to claim 6, wherein AA is β-Ala.

9. The compound according to claim 6, wherein AA is γ-Abu.

10. The compound according to claim 6, wherein AA is Ahx.

11. The compound according to claim 6, wherein AA is 4-Amb.

12. The compound according to claim 6, wherein AA is 4-Abz.

13. The compound according to claim 1, wherein at least one of R' is CH$_3$ or CF$_3$.

14. A pharmaceutical composition comprising the compound of claim 1 and a pharmaceutical-acceptable carrier.

15. A method for treating pain in a subject, said method comprising administering to the subject a therapeutically effective amount of the compound of claim 1.

* * * * *